United States Patent
Kano et al.

(10) Patent No.: US 11,437,129 B2
(45) Date of Patent: Sep. 6, 2022

(54) SUPPORTING APPARATUS, DISPLAY SYSTEM, AND SUPPORTING METHOD

(71) Applicant: Canon Medical Systems Corporation, Otawara (JP)

(72) Inventors: Yusuke Kano, Nasushiobara (JP); Anri Sato, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 188 days.

(21) Appl. No.: 16/579,325

(22) Filed: Sep. 23, 2019

(65) Prior Publication Data

US 2020/0105388 A1  Apr. 2, 2020

(30) Foreign Application Priority Data

Sep. 28, 2018 (JP) .............................. JP2018-184911

(51) Int. Cl.
| | |
|---|---|
| G16H 40/20 | (2018.01) |
| G16H 10/60 | (2018.01) |
| G16H 15/00 | (2018.01) |
| G06T 11/20 | (2006.01) |
| G16H 50/70 | (2018.01) |
| G06F 3/14 | (2006.01) |
| G06K 9/62 | (2022.01) |
| G16H 10/40 | (2018.01) |

(52) U.S. Cl.
CPC ............... *G16H 15/00* (2018.01); *G06F 3/14* (2013.01); *G06K 9/6267* (2013.01); *G06T 11/206* (2013.01); *G16H 10/40* (2018.01); *G16H 10/60* (2018.01); *G16H 40/20* (2018.01); *G16H 50/70* (2018.01)

(58) Field of Classification Search
CPC ........ G16H 15/00; G16H 10/40; G16H 10/60; G16H 40/20; G16H 50/70; G06F 3/14; G06K 9/6267; G06K 2209/05; G06T 11/206; G06V 2201/03
See application file for complete search history.

(56) References Cited

U.S. PATENT DOCUMENTS

2014/0092094 A1   4/2014 Itoh et al.
2016/0321404 A1*  11/2016 Ginsburg ............ G06F 3/04842
(Continued)

FOREIGN PATENT DOCUMENTS

| JP | 2014-71693 A | 4/2014 |
|---|---|---|
| JP | 2015-69446 A | 4/2015 |
| JP | 2016-184221 A | 10/2016 |

OTHER PUBLICATIONS

Office Action dated Apr. 19, 2022 in corresponding Japanese Patent Application No. 2018-184911, filed on Sep. 28, 2018 (3 pages).

*Primary Examiner* — Maroun P Kanaan
(74) *Attorney, Agent, or Firm* — Oblon, McClelland, Maier & Neustadt, L.L.P.

(57) ABSTRACT

In general, according to the present embodiment, a supporting apparatus includes processing circuitry. The processing circuitry extracts attributes concerning a plurality of medical examination data items of a patient, classifies the medical examination data items into a first group and a second group based on the attributes, and generates a display screen that displays the classified medical examination data items on a common time axis in display forms distinguishable between the groups.

15 Claims, 19 Drawing Sheets

(56) References Cited

U.S. PATENT DOCUMENTS

| | | | |
|---|---|---|---|
| 2018/0137249 A1* | 5/2018 | Eggebraaten | G16H 10/60 |
| 2020/0051697 A1* | 2/2020 | Krishnamurti | G06N 20/00 |
| 2021/0193304 A1* | 6/2021 | Ichiba | G06Q 10/105 |

* cited by examiner

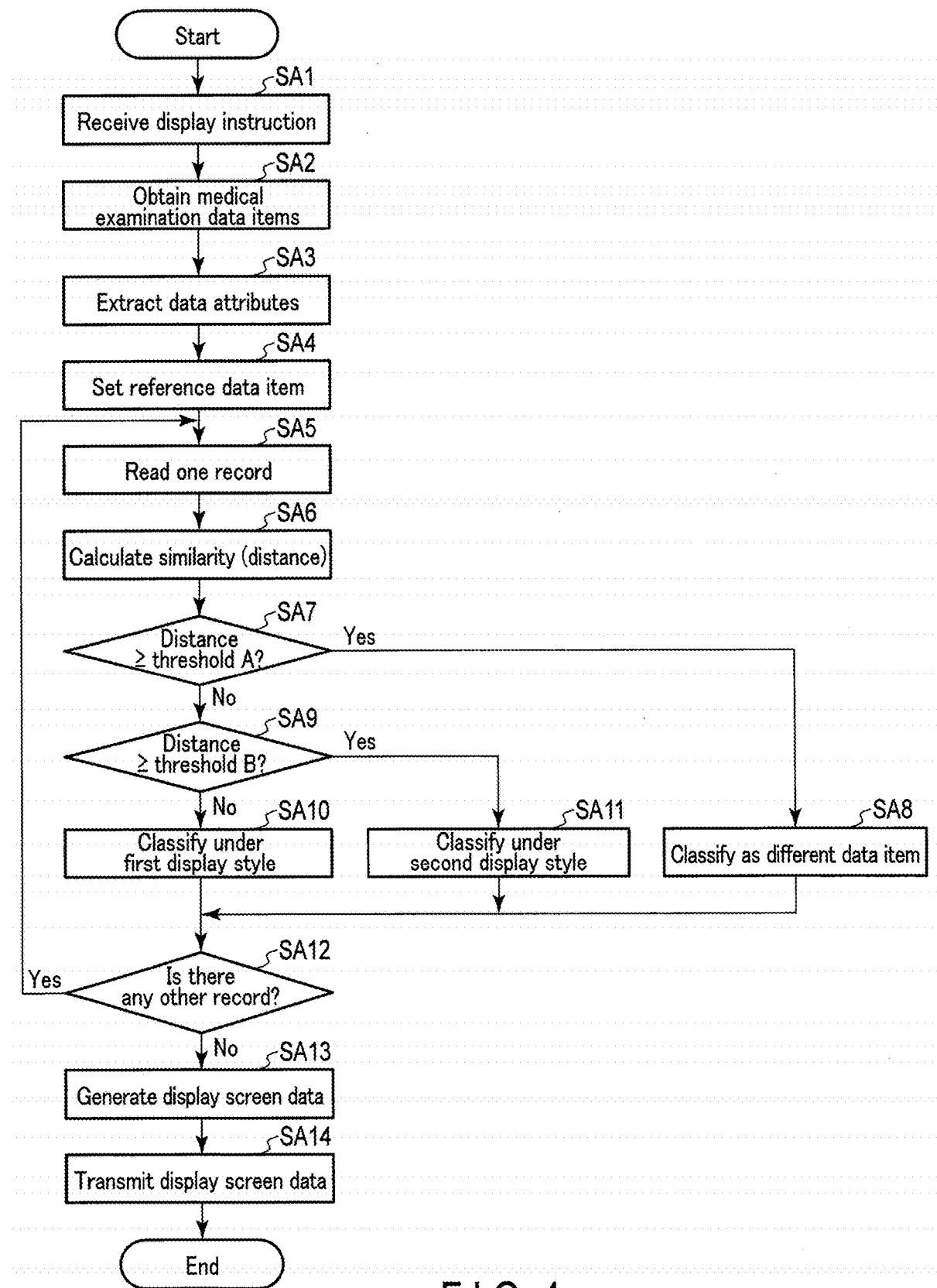
F I G. 4

| Patient ID | Item ID | Item name | Measurement time | Measurement | Unit |
|---|---|---|---|---|---|
| P0001 | 0001 | CREA | 20170511 21:30 | 0.29 | mg/dl |
| P0001 | 0001 | CREA | 20170515 09:00 | 0.36 | mg/dl |
| P0001 | 0001 | CREA | 20170517 14:45 | 0.83 | mg/dl |
| P0001 | 0010 | AST(GOT) | 20170426 09:15 | 46 | U/l |
| P0001 | 0010 | AST(GOT) | 20170428 15:30 | 28 | U/l |
| P0001 | 0010 | AST(GOT) | 20170501 10:15 | 3.6 | IU/l |
| P0001 | 0010 | AST(GOT) | 20170502 09:00 | 14 | U/l |
| P0001 | 0010 | AST(GOT) | 20170506 14:45 | 13 | U/l |
| P0001 | 0010 | AST(GOT) | 20170508 21:30 | 3.8 | IU/l |
| P0001 | 0010 | AST(GOT) | 20170510 21:30 | 4.5 | IU/l |
| P0001 | 0010 | AST(GOT) | 20170511 21:30 | 14 | U/l |
| P0001 | 0010 | AST(GOT) | 20170515 09:00 | 28 | U/l |
| P0001 | 0010 | AST(GOT) | 20170517 14:45 | 46 | U/ll |

F I G. 5

| Patient ID | Item ID | Item name | Measurement time | Measurement | Unit | Distance | Display method |
|---|---|---|---|---|---|---|---|
| P0001 | 0001 | CREA | 20170511 21:30 | 0.29 | mg/dl | 11 | CREA-first display |
| P0001 | 0001 | CREA | 20170515 09:00 | 0.36 | mg/dl | 11 | CREA-first display |
| P0001 | 0001 | CREA | 20170517 14:45 | 0.83 | mg/dl | 11 | CREA-first display |
| P0001 | 0010 | AST(GOT) | 20170426 09:15 | 46 | U/l | 0 | AST(GOT)-first display |
| P0001 | 0010 | AST(GOT) | 20170428 15:30 | 28 | U/l | 0 | AST(GOT)-first display |
| P0001 | 0010 | AST(GOT) | 20170501 10:15 | 3.6 | IU/l | 1 | AST(GOT)-second display |
| P0001 | 0010 | AST(GOT) | 20170502 09:00 | 14 | U/l | 0 | AST(GOT)-first display |
| P0001 | 0010 | AST(GOT) | 20170506 14:45 | 13 | U/l | 0 | AST(GOT)-first display |
| P0001 | 0010 | AST(GOT) | 20170508 21:30 | 3.8 | IU/l | 1 | AST(GOT)-second display |
| P0001 | 0010 | AST(GOT) | 20170510 21:30 | 4.5 | IU/l | 1 | AST(GOT)-second display |
| P0001 | 0010 | AST(GOT) | 20170511 21:30 | 14 | U/l | 0 | AST(GOT)-first display |
| P0001 | 0010 | AST(GOT) | 20170515 09:00 | 28 | U/l | 0 | AST(GOT)-first display |
| P0001 | 0010 | AST(GOT) | 20170517 14:45 | 46 | U/l | - | AST(GOT)-first display |

FIG. 6

| Measurement time | Measurement |
|---|---|
| 20170426 09:15 | - |
| 20170428 15:30 | + |
| 20170501 10:15 | 3.6 |
| 20170502 09:00 | ++ |
| 20170506 14:45 | ++ |
| 20170508 21:30 | 3.8 |
| 20170510 21:30 | 4.5 |
| 20170511 21:30 | + |
| 20170515 09:00 | - |
| 20170517 14:45 | - |
F I G. 10
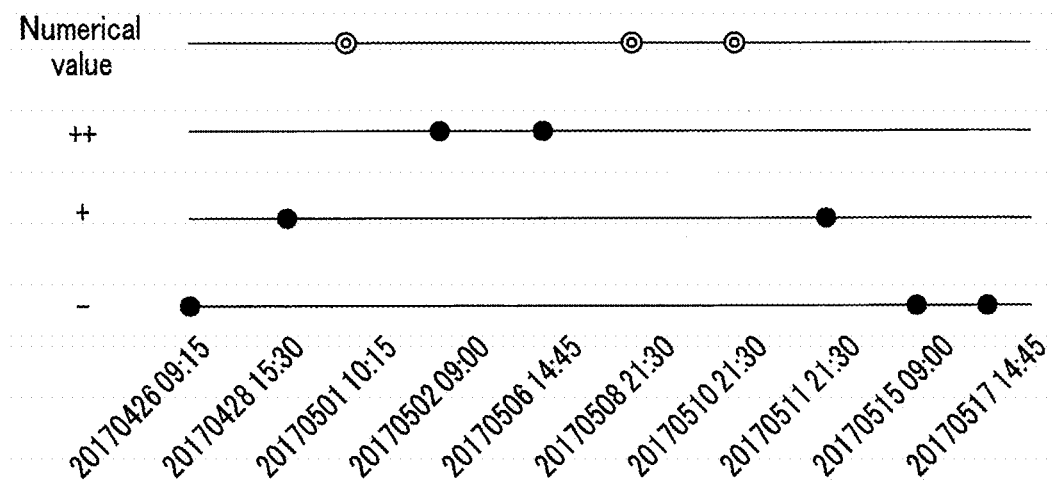
F I G. 11

| Patient ID | Item ID | Item name | Measurement time | Apparatus name | Tester | Measurement | Unit | Distance | Display method |
|---|---|---|---|---|---|---|---|---|---|
| P0001 | 0001 | LVIDd (2D) | 20170511 21:30 | Echo of manuf. A | Technician Y | 34 | mm | 10 | LVDd-second display |
| P0001 | 0001 | LVDd | 20170515 09:00 | Echo of manuf. A | Technician Y | 27 | mm | 10 | LVDd-second display |
| P0001 | 0001 | LVDd | 20170517 14:45 | Echo of manuf. A | Technician X | 20 | mm | 12 | LVDd-first display |
| P0001 | 0010 | LVIDd (M) | 20170420 00:00 | Echo of manuf. A | Technician Y | 36 | mm | 0 | LVIDd (M)-first display |
| P0001 | 0010 | LVIDd (M) | 20170426 09:15 | Echo of manuf. A | Technician X | 26 | mm | 2 | LVIDd (M)-second display |
| P0001 | 0010 | LVIDd (M) | 20170428 15:30 | Echo of manuf. B | Technician X | 29 | mm | 5 | Manuf. B LVIDd(M)-first display |
| P0001 | 0010 | LVIDd (M) | 20170429 10:15 | Echo of manuf. B | Technician X | 37 | mm | 5 | Manuf. B LVIDd(M)-first display |
| P0001 | 0010 | LVIDd (M) | 20170501 00:00 | Echo of manuf. A | Technician Y | 42 | mm | 0 | LVIDd (M)-first display |
| P0001 | 0010 | LVIDd (M) | 20170503 21:30 | Echo of manuf. A | Technician Y | 120 | mm | 1 | LVIDd (M)-second display |
| P0001 | 0010 | LVIDd (M) | 20170508 09:00 | Echo of manuf. A | Technician Y | 39 | mm | - | LVIDd (M)-first display |

F I G. 12

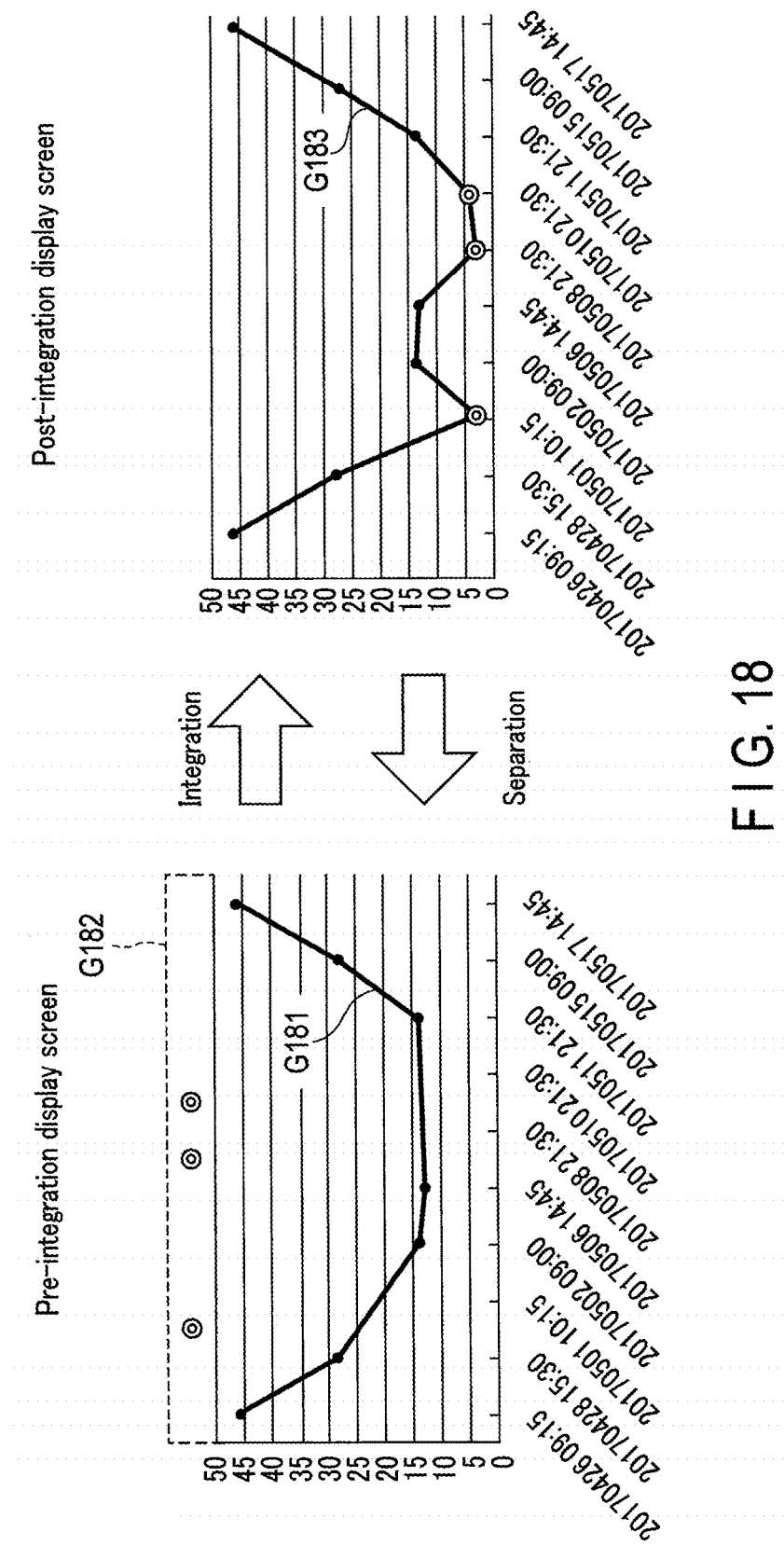
F I G. 18

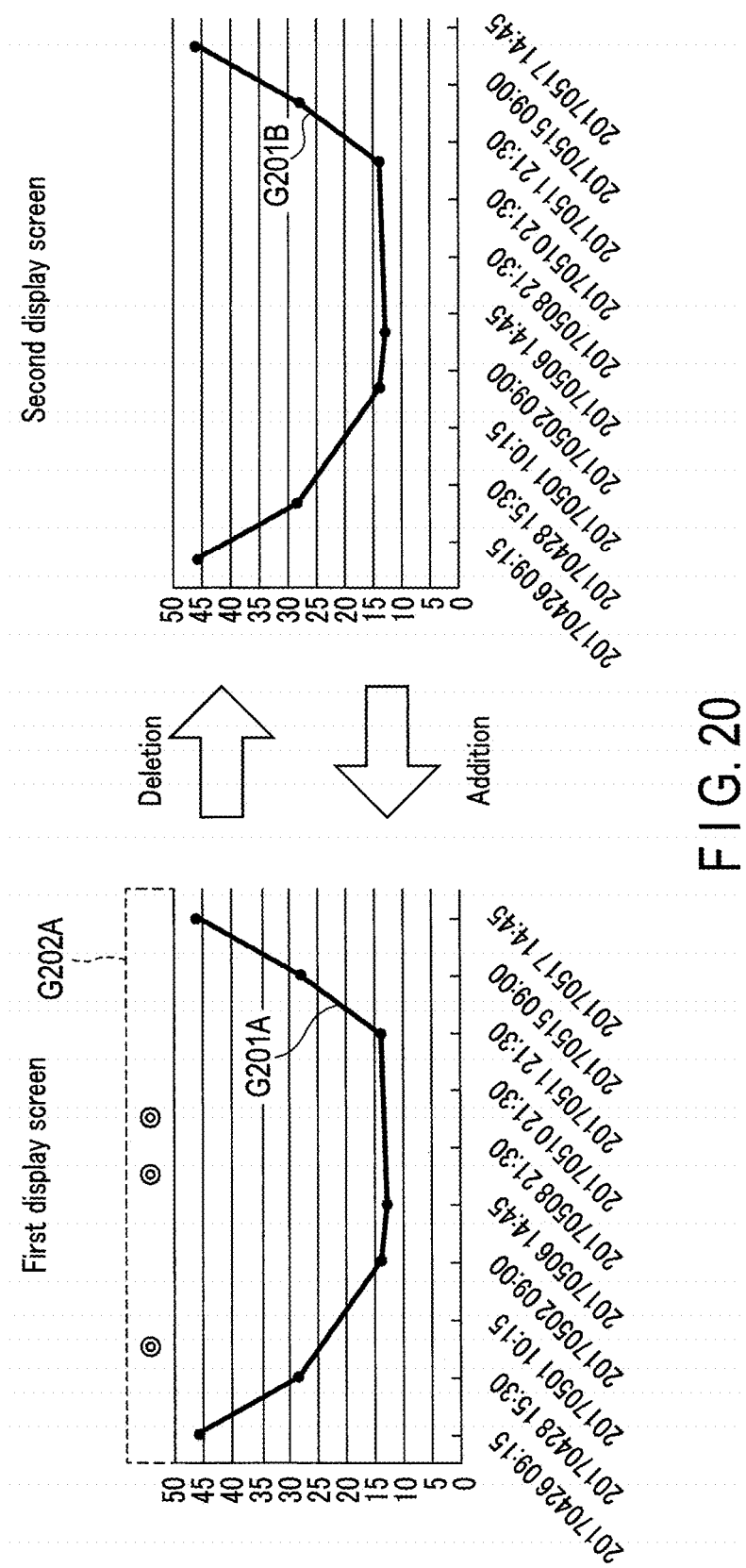
F I G. 20

# SUPPORTING APPARATUS, DISPLAY SYSTEM, AND SUPPORTING METHOD

CROSS-REFERENCE TO RELATED APPLICATIONS

This application is based upon and claims the benefit of priority from the prior Japanese Patent Application No. 2018-184911, filed Sep. 28, 2018, the entire contents of which are incorporated herein by reference.

FIELD

Embodiments generally relate to a supporting apparatus, a display system, and a supporting method.

BACKGROUND

In recent years, various types of medical examination data, such as a test result, are accumulated in a hospital. However, medical examination data accumulated in a hospital is a mixture of data obtained in different environments with different apparatuses and settings, etc., and the mixed medical examination data is not integratively managed.

If such medical examination data obtained in different environments is not integratively managed, for example, medical examination data obtained in a different environment from reference medical examination data may be handled as improper data including an improper value, and is partly or completely omitted when displayed as a medical examination screen. A user in visual contact with such a medical examination screen can recognize an existence of an error, but cannot ascertain whether or not the medical examination data missing on the medical examination screen is necessary for diagnosis because the improper data is not displayed as a graph or properly. Therefore, efficiency in ascertaining data obtained in various environments may decrease.

BRIEF DESCRIPTION OF THE DRAWINGS

FIG. 4 is a flowchart showing a flow of processing performed by the processing circuitry included in the medical server shown in FIG. 3.

FIG. 5 is a diagram showing medical examination data items each accompanied by a series of data attributes.

FIG. 6 is a diagram for explaining an operation of the processing circuitry included in the medical server shown in FIG. 3.

FIG. 10 is a diagram showing medical examination data items each accompanied by a series of data attributes in the first modification.

FIG. 11 is a diagram showing an example of the display screen displayed on the display of the medical terminal shown in FIG. 2 in the first modification.

FIG. 12 is a diagram for explaining an operation of the processing circuitry included in the medical server shown in FIG. 3 in the second modification.

FIG. 18 is a diagram for explaining other switching of display forms in the display screen displayed on the display of the medical terminal shown in FIG. 16.

FIG. 20 is a diagram for explaining other switching of display forms in the display screen displayed on the display of the medical terminal shown in FIG. 16.

DETAILED DESCRIPTION

In general, according to the present embodiments, a supporting apparatus includes processing circuitry. The processing circuitry extracts attributes concerning a plurality of medical examination data items of a patient, classifies the medical examination data items into a first group and a second group based on the attributes, and generates a display screen that displays the classified medical examination data items on a common time axis in display forms distinguishable between the groups.

First Embodiment

Hereinafter, a first embodiment will be described with reference to the drawings.

Figure 1:
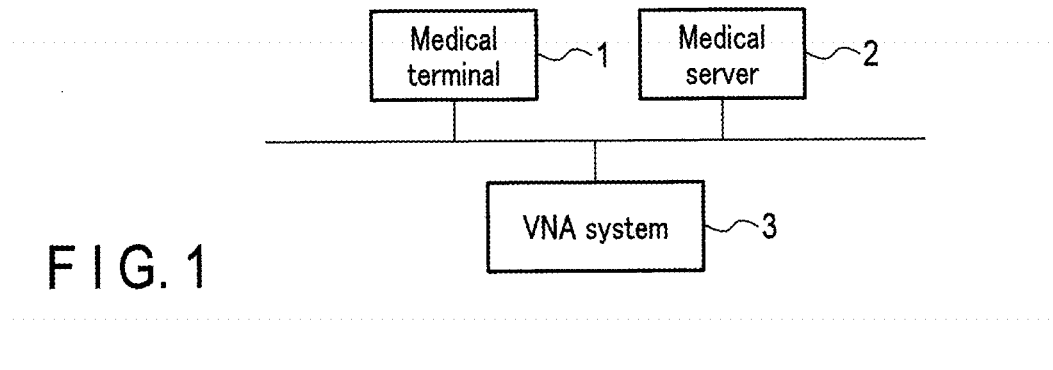
FIG. 1 is a block diagram showing a medical information system including a medical terminal and medical server according to the first embodiment.

FIG. 1 is a block diagram showing an example of the environment in which a medical terminal 1 and medical server 2 according to the first embodiment are used. The medical terminal 1 and medical server 2 shown in FIG. 1 constitute, for example, a client server system in which the medical terminal 1 functions as a client, and the medical server 2 functions as a server.

The medical terminal 1 shown in FIG. 1 is, for example, an apparatus capable of integratively observing medical information. For example, an integrative viewer is installed in the medical terminal 1. The integrative viewer is an application for integratively presenting medical information to the user. The integrative viewer may be embodied as, for example, a web application, a fat client application, or a thin client application.

The medical server 2 shown in FIG. 1 is an apparatus that receives a processing request from the medical terminal 1 and performs processing corresponding to the received processing request. A predetermined server application corresponding to the integrative viewer installed in the medical terminal 1 is installed in the medical server 2. The medical server 2 is an example of the medical information processing apparatus recited in the claims. The medical terminal 1 and medical server 2 are an example of the medical information processing system recited in the claims.

The medical terminal 1 and medical server 2 are connected to, for example, a vendor neutral archive (VNA) system 3 shown in FIG. 1 in a communicative manner via an intra-hospital network, such as a local area network (LAN).

The VNA system 3 shown in FIG. 1 is an integrative archive system that comprehensively manages medical image files stored in medical image management systems (picture archiving and communication systems: PACS) of different manufacturers and various medical examination data managed by respective clinical department systems. The VNA system 3 is connected to, for example, a PACS (not shown) and an electronic health record system (not shown) via an intra-hospital network, such as a LAN, in a communicative manner. For example, the VNA system 3 regularly obtains a medical image file stored in the PACS, and stores the medical image file in a memory included in the VNA system 3.

The medical image file is, for example, a file in a format based on the digital imaging and communication in medicine (DICOM) standard. The medical image file may be reworded as DICOM data. The medical image file is generated by a medical image diagnosis apparatus, which performs a test by, for example, imaging a patient. The medical image diagnosis apparatus generates the medical image file based on medical image data representing a medical image, which is generated as a result of the test. The medical image diagnosis apparatus includes, for example, an X-ray computed tomography apparatus, an X-ray diagnostic apparatus, a magnetic resonance imaging apparatus, a nuclear medicine diagnostic apparatus, and an ultrasound diagnostic apparatus.

The medical image file includes, for example, medical image data and attendant information. The attendant information is information for classifying the medical image data included in the medical image file, which indicates the source or the like of the medical image data. The attendant information includes information for specifying the medical image, such as a test unique identifier (UID), a series UID, a patient identifier (ID), a patient name, a birth date, a modality code, or a series description.

The test UID is an identifier capable of uniquely identifying a test. The series UID is an identifier capable of uniquely identifying a series of images obtained for, for example, each imaging site or imaging condition. The client ID is provided to each patient, and is an identifier for uniquely identifying the client in, for example, one hospital. The patient name represents a name of the patient corresponding to the patient ID. The birth date represents a birth date of the patient corresponding to the patient ID.

The modality code is an identifier for identifying a modality type, and defines, for example, "CT", "MR", or "US". The "CT", "MR", and "US" mean that the medical image is obtained by an X-ray computed tomography apparatus, a magnetic resonance imaging apparatus, and an ultrasound diagnostic apparatus, respectively. The series description represents a content of special note when there is a special note left by the laboratory technician for the doctor in the test (imaging).

The VNA system 3 also regularly obtains information on electronic health records stored in the electronic health record system, and stores the information in the memory included in the VNA system 3.

The information on electronic health record includes, for example, patient information and medical examination data. The patient information is information unique to the patient, and includes, for example, a patient ID, a patient name, a birth date, a gender, and an age.

The medical examination data is information on, for example, a patient's physical status, pathology, or treatment obtained by medical staff in the process of medical examination. The medical examination data includes data obtained in various environments, such as data obtained by apparatuses of different manufacturers, data obtained by apparatuses of different versions, or data obtained by the same apparatus, but with different settings. The medical examination data is not limited to objective data such as a numerical value, but may be a non-numerical value, such as objective data represented by letters/characters.

The medical examination data includes, for example, test history information, image information, electrocardiographic information, vital sign information, medication history information, report information, health record description information, or nursing record information.

The test history information is, for example, information representing history of test results obtained as a result of a laboratory test, a bacteria test, or the like on the patient.

The image information is, for example, information representing the location of a medical image obtained, for example, by imaging the patient. The image information includes, for example, information representing the location of a medical image file generated by the medical image diagnosis apparatus as a result of a test.

The electrocardiographic information is, for example, information on an electrocardiographic waveform measured from the patient.

The vital sign information is, for example, basic information relating to a patient's life. The vital sign information includes, for example, a pulse rate, a respiration rate, a body temperature, a blood pressure, and a level of consciousness.

The medication history information is, for example, information indicating a history of quantities of medication given to the patient.

The report information is, for example, information on a summary of the condition and disease of the patient made by a radiologist in the radiology department interpreting a medical image such as an X-ray image, a CT image, an MRI image, or an ultrasonic image in response to a test request from a clinician in the clinical department. The report information includes, for example, interpretation report information representing an interpretation report made by a radiologist with reference to a medical image file stored in the PACS. The report information includes, for example, information representing a patient ID, patient name, and birth date of a patient corresponding to the medical image file to be interpreted.

The health record description information is, for example, information input to the electronic health record by a clinician, etc. The health record description information includes, for example, a medical examination record on admission, patient's medical history, and prescribed medication history.

The nursing record information is, for example, information input to the electronic health record by a nurse, etc. The nursing record information includes a nursing record, etc. on admission.

Figure 2:
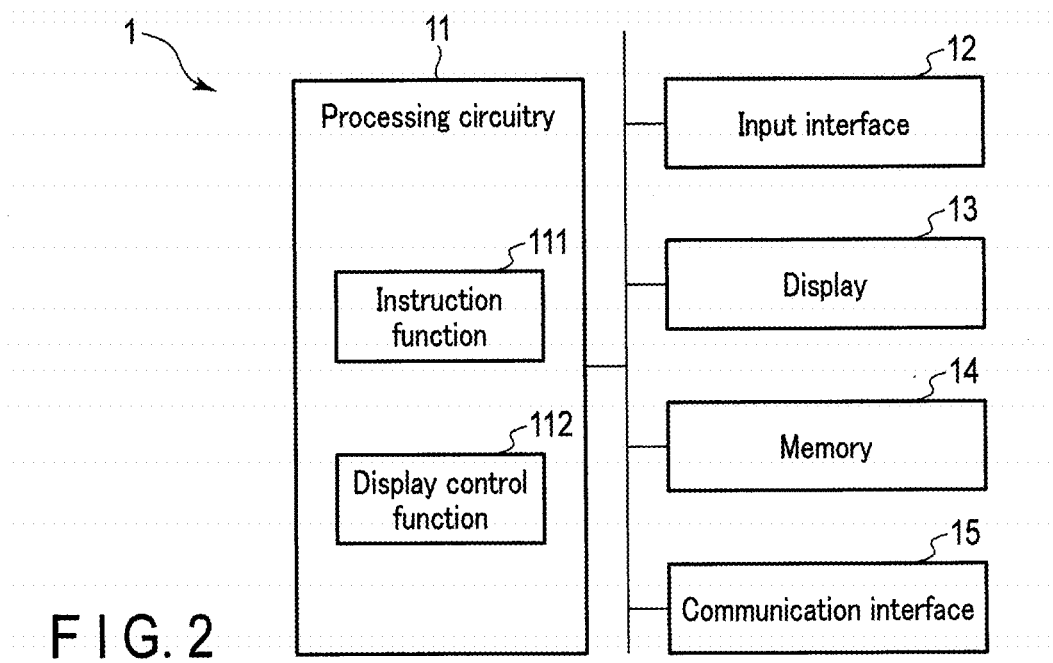
FIG. 2 is a block diagram showing a functional configuration of the medical terminal shown in FIG. 1.
Figure 3:
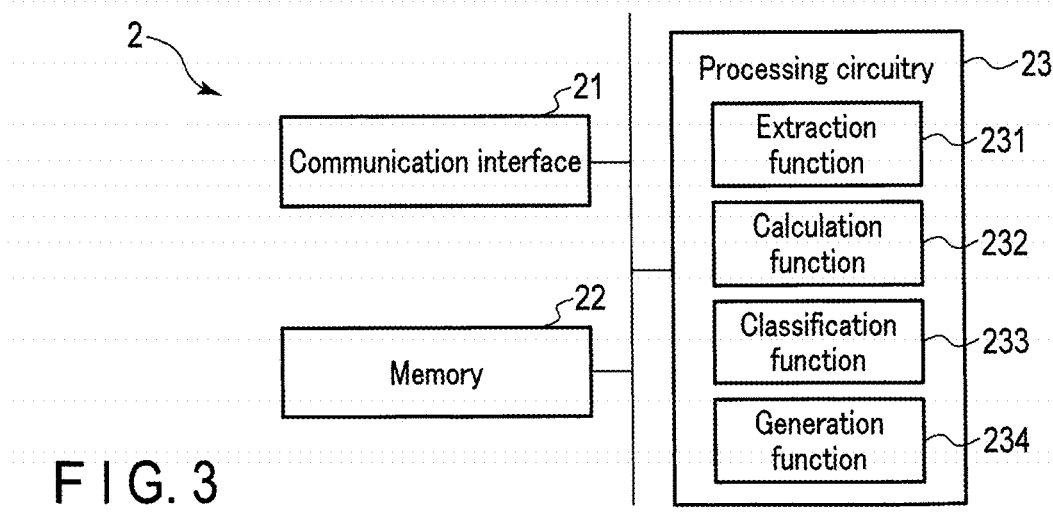
FIG. 3 is a block diagram showing a functional configuration of the medical server shown in FIG. 1.

Next, details of the medical terminal 1 and medical server 2 according to the first embodiment will be described with reference to FIGS. 2 and 3. FIG. 2 is a block diagram showing a functional configuration of the medical terminal 1 shown in FIG. 1. FIG. 3 is a block diagram showing a functional configuration of the medical server 2 shown in FIG. 1.

The medical terminal 1 shown in FIG. 2 includes processing circuitry 11, an input interface 12, a display 13, a memory 14, and a communication interface 15. The processing circuitry 11, the input interface 12, the display 13, the memory 14, and the communication interface 15 are connected via, for example, a bus in a communicative manner.

The processing circuitry 11 is a processor that functions as a nerve center of the medical terminal 1. The processing circuitry 11 executes a control program stored in, for example, the memory 14, thereby realizing a function corresponding to the program.

The input interface 12 is implemented by, for example, a mouse, a keyboard, or a touch pad to which an instruction is input by the operator touching the operation screen. The input interface 12 receives, for example, a display instruction from the operator. The input interface 12 converts the display instruction from the operator into an electrical signal, and outputs the electrical signal to the processing circuitry.

The display 13 displays various information to allow the user to perform various operations. As the display 13, for example, a CRT display, a liquid crystal display, an organic EL display, an LED display, a plasma display, or any other display known in the relevant technical field may be used as appropriate.

The memory 14 is a storage device, such as a hard disk drive (HDD), a solid state drive (SSD), or an integrated circuit storage device, etc., which stores various information. The memory 14 may be, for example, a CD-ROM drive, a DVD drive, or a drive which reads and writes various information from and in a portable storage medium, such as a flash memory. The memory 14 stores, for example, various control programs performed by the processing circuitry 11.

The communication interface 15 performs data communication between the medical server 2 and VNA system 3 connected via an intra-hospital network. The standard of the communication with the medical server 2 and the VNA system 3 may be any standard, but is, for example, HL7, DICOM, or both.

The processing circuitry 11 according to the first embodiment has an instruction function 111 and a display control function 112.

The instruction function 111 is a function of transmitting a predetermined instruction to the medical server 2. By executing the instruction function 111, the processing circuitry 11 receives, for example, a display instruction to display medical examination data concerning a specific patient, and transmits the received display instruction to the medical server 2. The display instruction is, for example, input via the input interface 12, and transmitted via the communication interface 15.

The display control function 112 is a function of displaying the medical examination data. By executing the display control function 112, the processing circuitry 11 causes the display 13 to display medical examination data in a predetermined display style based on the processing result transmitted from the medical server 2.

The instruction function 111 and display control function 112 may be incorporated in the processing circuitry 11 as control programs or as dedicated hardware circuits capable of performing respective functions.

The medical server 2 according to the first embodiment determines, for example, the display form of medical examination data to be displayed on the display of the medical terminal 1. FIG. 3 is a block diagram showing a functional configuration of the medical server 2 shown in FIG. 1. The medical server 2 shown in FIG. 3 includes a communication interface 21, a memory 22, and processing circuitry 23.

The communication interface 21 performs data communication with external apparatuses, such as the medical server 1 and VNA system 3, connected via the network or the like, which are shown in FIG. 1.

The memory 22 is a storage device, such as an HDD, an SSD, or an integrated circuit storage device, which stores various information. The memory 22 may be, for example, a CD-ROM drive, a DVD drive, or a drive which reads and writes various information from and in a portable storage medium, such as a flash memory. The memory 22 stores, for example, a medical image file and medical examination data.

The processing circuitry 23 is a processor that functions as a nerve center of the medical server 2. The processing circuitry 23 also implements various functions shown in FIG. 3 by executing operation programs read from the memory 22. Specifically, the processing circuitry 23 has an extraction function 231, a calculation function 232, a classification function 233, and a generation function 234.

The extraction function 231 is a function of extracting an attribute relating to medical examination data stored in relation to the patient. By executing the extraction function 231, the processing circuitry 23 receives, for example, a display instruction to display medical examination data, and obtains medical examination data. The processing circuitry 23 extracts a series of preset data attributes from the obtained medical examination data.

The data attributes are elements indicating, for example, various attributes relating to various medical examination data obtained from the patient. The data attributes include, for example, a patient ID, an item ID, an item name, a measurement time, an apparatus name, a tester, and a unit representing a measurement unit. The data attributes may include a measurement condition. The data attributes may include not only a name, but also a predetermined ID or the like as long as it allows identification.

One series of data attributes are stored in association with each medical examination data item. The medical examination data item is data including at least one measurement, medical image data item, or the like obtained from the patient in, for example, a laboratory test or an imaging test.

The calculation function 232 is a function of calculating a similarity between a designated medical examination data item and another medical examination data item of a plurality of stored medical examination data items. By executing the calculation function 232, the processing circuitry 23 sets, for example, one medical examination data item of a plurality of medical examination data items as a reference data item. For example, the processing circuitry 23 sets the medical examination data item having the most recent measurement time as the reference data item. The processing circuitry 23 calculates a similarly between the medical examination data item set as the reference data item and another medical examination data item.

The similarity is calculated based on, for example, data attributes of the medical examination data item. Specifically, the similarity is expressed by, for example, a distance between the reference data item and the other medical examination data item. For example, the processing circuitry 23 compares the data attributes accompanying the reference data item with the data attributes accompanying the other medical examination data item, and calculates a distance between the reference data item and the medical examination data item based on the differences between the data attributes. More specifically, the processing circuitry 23 calculates the distance between the reference data item and the other medical examination data item based on, for example, the difference between data item names, the difference between obtained units, and the difference between the accuracies attributed to apparatuses. The distance is calculated based on, for example, scores which are obtained in advance by converting the difference between data attributes into numerical values for each data attribute.

The classification function 233 is a function of classifying a medical examination data item based on the similarity. By executing the classification function 233, the processing circuitry 23 classifies a medical examination data item into at least one of a plurality of classification groups by using, for example, the distance calculated by the calculation function 232. Specifically, the processing circuitry 23 compares the distance calculated by the calculation function 232 with a predetermined threshold, thereby classifying a medical examination data item into at least one of a plurality of classification groups.

The generation function 234 is a function of generating display screen data representing a display screen of a graph of classified medical examination data items with a common time axis. By executing the generation function 234, the processing circuitry 23 generates display screen data of a graph in which medical examination data items classified into the same classification group as the reference data item are shown in a display form (display style) that distinguishes the classification group from the other classification groups. For example, the processing circuitry 23 displays the medical examination data items and the reference data item by one graph in a predetermined region. The processing circuitry 23 also generates display screen data so that medical examination data items classified into a different classification group from the reference data item are displayed by a display form different from that of the medical examination data items classified into the same classification group as the reference data item.

The operation of the processing circuitry 23 of the medical server 2 which is configured as described above will be described in accordance with the procedure shown in FIG. 4.

The following description will be provided on the assumption that a display instruction to display a display screen concerning medical examinations of a specific patient is input via the input interface 12 of the medical terminal 1, and the input display instruction is transmitted from the medical terminal 1 to the medical server 2.

FIG. 4 is a flowchart showing a flow of processing performed by the processing circuitry 23 included in the medical server 2 shown in FIG. 3.

In FIG. 4, the processing circuitry 23, for example, receives a display instruction to display a display screen concerning medical examinations from the medical terminal 1 via the communication interface 21 (step SA1).

Upon receipt of the display instruction to display a medical examination screen, the processing circuitry 23, for example, obtains medical examination data items from the VNA system 3 by using information indicating a specific patient, which is included in the display instruction, as a key (step SA2).

The processing circuitry 23 extracts data attributes from each of the obtained medical examination data item (step SA3). A medical examination data item accompanied by a sequence of data attributes is thereby generated. FIG. 5 is a diagram showing an example of the medical examination data items each accompanied by a series of data attributes. FIG. 5 shows 13 medical examination data items. According to FIG. 5, each medical examination data item includes, for example, a measurement, and data attributes accompanying the measurement. The data attributes shown in FIG. 5 include a patient ID, an item ID indicating an ID for identifying a test item, an item name indicating a name of the test item, a measurement time, a unit, etc.

The set of medical examination data items shown in FIG. 5 includes, for example: a medical examination data item constituted by patient ID "P0001", item ID "0001", item name "CREA", measurement time "2017051121:30", measurement "0.29", and unit "mg/dl"; a medical examination data item constituted by patient ID "P0001", item ID "0001", item name "CREA", measurement time "20170515 09:00", measurement "0.36", and unit "mg/dl"; a medical examination data item constituted by patient ID "P0001", item ID "0001", item name "CREA", measurement time "20170517 14:45", measurement "0.83", and unit "mg/dl"; a medical examination data item constituted by patient ID "P0001", item ID "0010", item name "AST(GOT)", measurement time "20170426 09:15", measurement "46", and unit "U/I"; a medical examination data item constituted by patient ID "P0001", item ID "0010", item name "AST (GOT)", measurement time "20170428 15:30", measurement "28", and unit "U/I"; a medical examination data item constituted by patient ID "P0001", item ID "0010", item name "AST(GOT)", measurement time "20170501 10:15", measurement "3.6", and unit "IU/I"; a medical examination data item constituted by patient ID "P0001", item ID "0010", item name "AST(GOT)", measurement time "20170502 09:00", measurement "14", and unit"U/I"; a medical examination data item constituted by patient ID "P0001", item ID "0010", item name "AST(GOT)", measurement time "20170506 14:45", measurement "13", and unit "U/I"; a medical examination data item constituted by patient ID "P0001", item ID "0010", item name "AST (GOT)", measurement time "20170508 21:30", measurement "3.8", and unit "IU/I"; a medical examination data item constituted by patient ID "P0001", item ID "0010", item name "AST(GOT)", measurement time "20170510 21:30", measurement "4.5", and unit"IU/I"; a medical examination data item constituted by patient ID "P0001", item ID "0010", item name "AST(GOT)", measurement time "20170511 21:30", measurement "14", and unit "U/I"; a medical examination data item constituted by patient ID "P0001", item ID "0010", item name "AST(GOT)", measurement time "20170515 09:00", measurement "28", and unit "U/I"; and a medical examination data item constituted by patient ID "P0001", item ID "0010", item name "AST (GOT)", measurement time "20170517 14:45", measurement "46", and unit "U/I".

The processing circuitry 23 sets, as a reference data item, one medical examination data item having the most recent measurement time "20170517 14:45" of the medical examination data items having item name "AST(GOT)" (item ID "0010") among the medical examination data items shown in FIG. 5 (step SA4). The item name is determined, for example, by user's designation via the input interface 12.

Upon completion of the processing of setting the reference data item, the processing circuitry 23 reads one medical examination data item (one record) from the medical examination data items shown in FIG. 5 other than the medical examination data item set as the reference data item (step SA5). The processing circuitry 23 reads, for example, the medical examination data item with item ID "0001" and measurement time "20170511 21:30" shown in FIG. 5.

The processing circuitry 23 calculates a similarly between the medical examination data item set as the reference data item and the one read medical examination data item (step SA6). For example, the processing circuitry 23 compares data attributes "item ID" and "unit" accompanying the reference data item with data attributes "item ID" and "unit" accompanying the one read medical examination data item, respectively, and calculates a similarity, e.g., distance, between the data items based on the differences between data attributes.

FIG. 6 is a diagram for explaining an operation of the processing circuitry 23 included in the medical server 2 shown in FIG. 3. In FIG. 6, let us assume that the distance of when data attribute "patient ID" is different, the distance of when data attribute "item ID" is different, and the distance of when data attribute "unit" is different are set in advance as "20", "10", and "1", respectively, by a predetermined method. Instead of the distance of when data attribute "item ID" is different, the distance of when data attribute "item name" is different may be set as "10". In the following description, let us assume that the medical examination data items which are indicated by the display instruction are those of the same patient ID, and there is no difference in the patient ID between the medical examination data items.

As shown in FIG. 6, the processing circuitry 23 calculates a similarity between the reference data item and another medical examination data item by adding up the preset distances regarding respective data attributes in accordance with whether or not there is a difference in each data attribute. Specifically, since data attribute "item ID" of the medical examination data item set as the reference data item is "0010" and that of the read medical examination data item is "0001", which is different from "0010", the processing circuitry 23 adds "10" as a distance between data items to, for example, "0" as the initial value of the distance between data items. In addition, since data attribute "unit" of the medical examination data item set as the reference data item is "U/l" and that of the read medical examination data item is "mg/dl", which is different from "U/l", the processing circuitry 23 adds "1" as a distance between data items. Accordingly, the total distance between the medical examination data item set as the reference data item and the one read medical examination data item is calculated to be "11", as shown in FIG. 6. The processing for calculating a similarity in step SA6 in FIG. 4 is thereby finished.

The processing circuitry 23 determines whether or not the calculated distance is larger than predetermined threshold A (step SA7). The predetermined threshold A is, for example, 10. Since the calculated distance is "11", the processing circuitry 23 determines that the calculated distance is larger than the threshold A (Yes in step SA7), and classifies the medical examination data item with measurement time "20170511 21:30" as a medical examination data item different from the reference data item (step SA8). The processing circuitry 23, for example, classifies the medical examination data item with item ID "0001" and measurement time and date "20170511 21:30" as "CREA-first display" as shown in FIG. 6. "CREA-first display" indicates that, for example, the medical examination data item with item name "CREA" (item ID "0001") is classified under the first display style. The medical examination data items classified under "CREA-first display" are displayed, for example, on the display 13 of the medical terminal 1 in a form distinguishable from the form of the medical examination data items with an item name (item ID) different from "CREA". Regarding the medical examination data items classified under "CREA-first display", for example, medical examination data items with item name "CREA" are displayed, for example, on the display 13 in a form distinguishable from the form of the medical examination data items classified under another display style.

The processing circuitry 23 classifies in advance the reference data item as, for example, "AST(GOT)-first display" as shown in FIG. 6. "AST(GOT)-first display" indicates that, for example, the medical examination data item with item name "AST(GOT)" (item ID "0010") is classified under the first display style. The medical examination data items classified under "AST(GOT)-first display" are displayed, for example, on the display 13 in a form distinguishable from the form of the medical examination data items with an item name (item ID) different from "AST(GOT)". Regarding the medical examination data items classified under "AST(GOT)-first display", for example, the medical examination data items with item name "AST(GOT)" are displayed, for example, on the display 13 in a form distinguishable from the form of the medical examination data items classified under another display style.

The processing circuitry 23 determines whether or not there is any other record left after performing the processing for classifying a medical examination data item in step SA8 (step SA12).

Since there are still eleven medical examination data items to be compared with the reference data item (Yes in step SA12), the processing circuitry 23 reads one medical examination data item of the remaining medical examination data items (step SA5). The processing circuitry 23 reads, for example, the medical examination data item with item ID "0001" and measurement time "20170515 09:00" shown in FIG. 5.

The processing circuitry 23 calculates a similarly between the medical examination data item set as the reference data item and the read medical examination data item (step SA6). As in the case of the medical examination data item with measurement time "20170511 21:30", the total distance between the medical examination data item set as the reference data item and the read medical examination data item with item ID "0001" and measurement time "20170515 09:00" is calculated to be "11" as shown in FIG. 6. The processing for calculating a similarity in step SA6 shown in FIG. 4 is thereby finished.

The processing circuitry 23 determines whether or not the calculated distance is larger than predetermined threshold A (step SA7). The processing circuitry 23 determines that the calculated distance "11" is larger than the threshold A (Yes in step SA7) and, for example, classifies the medical examination data item with item ID "0001" and measurement time "20170515 09:00" as "CREA-first display" as shown in FIG. 6.

The processing circuitry 23 determines whether or not there is any other record left after performing the processing for classifying a medical examination data item in step SA8 (step SA12).

Since there are still ten medical examination data items to be compared with the reference data item (Yes in step SA12), the processing circuitry 23 reads one medical examination data item of the remaining medical examination data items (step SA5). The processing circuitry 23 reads, for example, the medical examination data item with item ID "0001" and measurement time "20170517 14:45" shown in FIG. 5.

The processing circuitry 23 calculates a similarly between the medical examination data item set as the reference data item and the read medical examination data item (step SA6). As in the case of the medical examination data item with item ID "0001" and measurement time "2017051121:30", the total distance between the medical examination data item set as the reference data item and the read medical examination data item with item ID "0001" and measurement time "20170517 14:45" is calculated to be "11" shown in FIG. 6. The processing for calculating a similarity in step SA6 shown in FIG. 4 is thereby finished.

The processing circuitry 23 determines whether or not the calculated distance is larger than predetermined threshold A (step SA7). The processing circuitry 23 determines that the calculated distance "11" is larger than the threshold A (Yes in step SA7) and, for example, classifies the medical examination data item with item ID "0001" and measurement time "20170515 09:00" as "CREA-first display" as shown in FIG. 6.

The processing circuitry 23 determines whether or not there is any other record left after performing the processing for classifying a medical examination data item in step SA8 (step SA12).

Since there are still nine medical examination data items to be compared with the reference data item (Yes in step SA12), the processing circuitry 23 reads one medical examination data item of the remaining medical examination data items (step SA5). The processing circuitry 23 reads, for example, the medical examination data item with item ID "0010" and measurement time "20170426 09:15" shown in FIG. 5.

Since data attribute "item ID" of the medical examination data item set as the reference data item and that of the read medical examination data item are the same "0010", and data attribute "unit" of the medical examination data item set as the reference data item and that of the read medical examination data item are the same "U/I" as shown in FIG. 6, the processing circuitry 23 calculates the distance between data items to be "0" (step SA6).

The processing circuitry 23 determines whether or not the calculated distance is larger than predetermined threshold A (step SA7).

The processing circuitry 23 determines that the calculated distance "0" is not larger than the threshold A, i.e., equal to or smaller than the threshold A (No in step SA7), and determines whether or not the calculated distance is larger than predetermined threshold B (step SA8). The predetermined threshold B is, for example, 0.

The processing circuitry 23 determines that the calculated distance "0" is not larger than the threshold B, i.e., equal to or smaller than the threshold B (No in step SA8) and, for example, classifies the medical examination data item with item ID "0010" and measurement time "20170426 09:15" as "AST(GOT)-first display" as shown in FIG. 6 (step SA10).

The processing circuitry 23 determines whether or not there is any other record left after performing the processing for classifying a medical examination data item in step SA10 (step SA12).

Since there are still eight medical examination data items to be compared with the reference data item (Yes in step SA12), the processing circuitry 23 reads one medical examination data item of the remaining medical examination data items (step SA5). The processing circuitry 23 reads, for example, the medical examination data item with item ID "0010" and measurement time "20170428 15:30" shown in FIG. 5.

Since data attribute "item ID" of the medical examination data item set as the reference data item and that of the read medical examination data item are the same "0010", and data attribute "unit" of the medical examination data item set as the reference data item and that of the read medical examination data item are the same "U/I" as shown in FIG. 6, the processing circuitry 23 calculates the distance between data items to be "0" (step SA6).

The processing circuitry 23 determines whether or not the calculated distance is larger than predetermined threshold A (step SA7).

The processing circuitry 23 determines that the calculated distance "0" is not larger than the threshold A, i.e., equal to or smaller than the threshold A (No in step SA7), and determines whether or not the calculated distance is larger than predetermined threshold B (step SA8).

The processing circuitry 23 determines that the calculated distance "0" is not larger than the threshold B, i.e., equal to or smaller than the threshold B (No in step SA8) and, for example, classifies the medical examination data item with item ID "0010" and measurement time and date "20170428 15:30" under "AST(GOT)-first display" as shown in FIG. 6 (step SA10).

The processing circuitry 23 determines whether or not there is any other record left after performing the processing for classifying a medical examination data item in step SA10 (step SA12).

Since there are still seven medical examination data items to be compared with the reference data item (Yes in step SA12), the processing circuitry 23 reads one medical examination data item of the remaining medical examination data items (step SA5). The processing circuitry 23 reads, for example, the medical examination data item with item ID "0010" and measurement time "20170501 10:15" shown in FIG. 5.

Since data attribute "item ID" of the medical examination data item set as the reference data item and that of the read medical examination data item are the same "0010", but data attribute "unit" of the medical examination data item set as the reference data item is "U/I" and that of the read medical examination data item is "IU/I", which is different from "U/I" as shown in FIG. 6, the processing circuitry 23 calculates the distance between data items to be "1" (step SA6).

The processing circuitry 23 determines whether or not the calculated distance is larger than predetermined threshold A (step SA7).

The processing circuitry 23 determines that the calculated distance "0" is not larger than the threshold A, i.e., equal to or smaller than the threshold A (No in step SA7), and determines whether or not the calculated distance is larger than predetermined threshold B (step SA8).

The processing circuitry 23 determines that the calculated distance "1" is larger than threshold B (Yes in step SA8) and, for example, classifies the medical examination data item with item ID "0010" and measurement time "20170501 10:15" under "AST(GOT)-second display" as shown in FIG. 6 (step SA10). "AST(GOT)-second display" indicates that, for example, the medical examination data item with item name "AST(GOT)" (item ID "0010") is classified under the second display style. The medical examination data item classified under "AST(GOT)-second display" is displayed in a form distinguishable from the form of, for example, the medical examination data items with an item name (item ID) different from "AST(GOT)". Regarding the medical examination data items classified under "AST(GOT)-second display", for example, medical examination data items with item name "AST(GOT)" are displayed in a form distinguishable from the form of the medical examination data items classified under another display style such as "AST(GOT)-first display". The processing circuitry 23 determines whether or not there is any other record left after performing the processing for classifying a medical examination data item in step SA10 (step SA12).

Similarly, since there are still seven medical examination data items to be compared with the reference data item (Yes in step SA12), the processing circuitry 23 repeats steps SA5 to SA12 for the remaining seven medical examination data items. Accordingly, as shown in FIG. 6, the medical examination data item with item ID "0010" and measurement time "20170502 09:00", the medical examination data item with item ID "0010" and measurement time "20170506 14:45", the medical examination data item with item ID "0010" and measurement time "20170508 21:30", the medical examination data item with item ID "0010" and measurement time "20170510 21:30", the medical examination data item with item ID "0010" and measurement time "20170511 21:30", and the medical examination data item with item ID "0010" and measurement time and date "20170515 09:00" are classified under "AST(GOT)-first display", "AST(GOT)-first display", "AST(GOT)-second display", "AST(GOT)-second display", "AST(GOT)-first display", and "AST(GOT)-first display", respectively.

After performing the processing for classifying twelve medical examination data items in this way, the processing circuitry 23 determines whether or not there is any other record left (step SA12).

Since there is no other medical examination data item to be compared with the reference data item (No in step SA12), the processing circuitry 23 generates display screen data based on the classification results of the medical examination data items obtained by the classification function 233 (step SA13). The display screen data represents a display screen of a graph in which medical examination data items classified under display forms (display styles) distinguishable between classification groups are plotted on a common time axis. The processing circuitry 23, for example, generates display screen data for each item name because there are medical examination data items of a plurality of item names as shown in FIG. 5.

The processing circuitry 23 transmits the generated display screen data to the medical terminal 1 via, for example, the communication interface 21 (step SA14).

The processing circuitry 11 included in the medical terminal 1 receives display screen data transmitted from the medical server 2. Then, the processing circuitry 11 receives designation of an item name (test item) of a display subject via, for example, the input interface 12. Upon receipt of designation of an item name of a display subject, for example, designation of item name "AST(GOT)", the processing circuitry 11 executes the display control function 112, thereby causing the display 13 to display a display screen based on the display screen data corresponding to item name "AST(GOT)".

Figure 7:
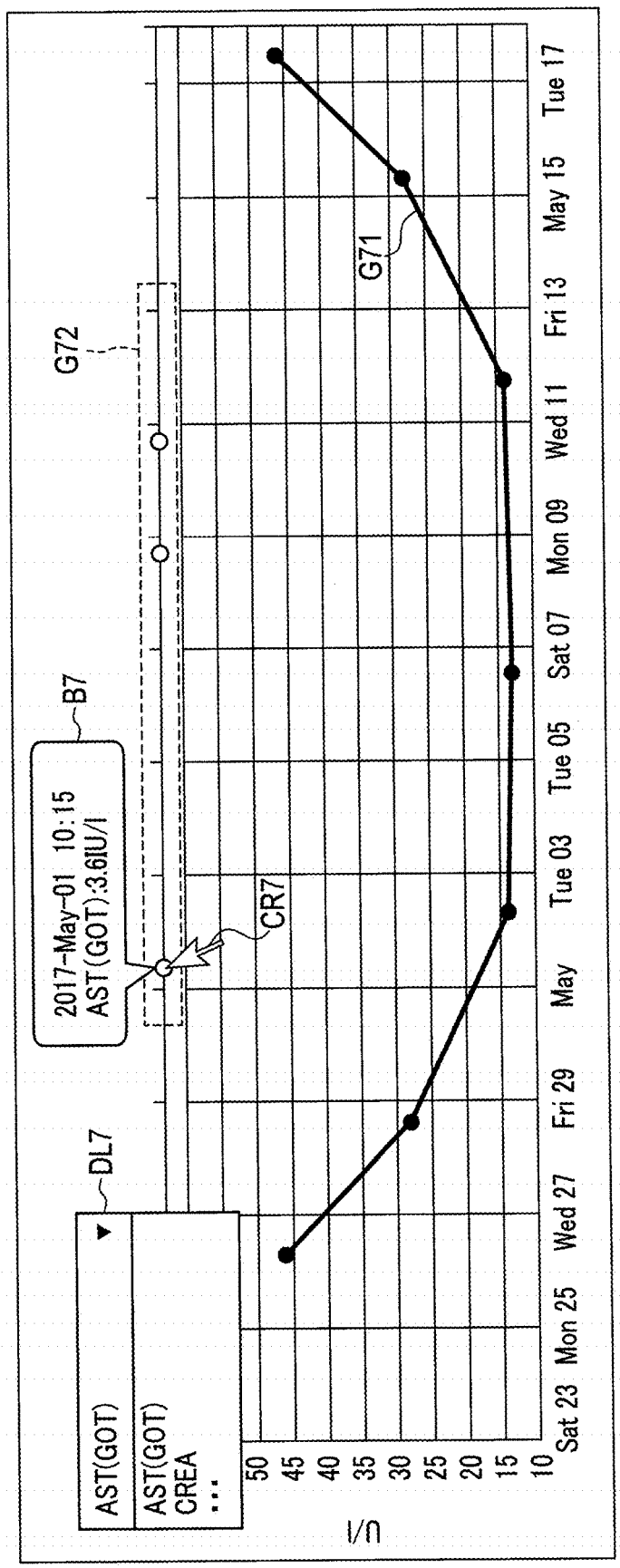
FIG. 7 is a diagram showing an example of the display screen displayed on the display of the medical terminal shown in FIG. 2.

FIG. 7 is a diagram showing an example of the display screen displayed on the display 13 of the medical terminal 1 shown in FIG. 2. The medical examination data items shown in FIG. 7 represent results of laboratory tests for, for example, patient ID "P0001". In the case of FIG. 7, for example, when one of the item names included in the drop-down list DL7 is designated, the processing circuitry 11 causes the display 13 to display test results corresponding to the designated item name.

With the drop-down list DL7 shown in FIG. 7, the display subject can be switched between, for example, "AST(GOT)" and "CREA". "AST(GOT)" indicates that, for example, medical examination data items with item name "AST (GOT)" are display subjects. "CREA" indicates that, for example, the medical examination data items with item name "CREA" are display subjects. In the case of FIG. 7, "AST(GOT)" is designated. Therefore, in FIG. 7, the processing circuitry 11 causes the display 13 to display the results of laboratory tests corresponding to the designated "AST(GOT)".

According to FIG. 7, the processing circuitry 11 causes the display 13 to display the medical examination data items classified under "AST(GOT)-first display" as graph G71. In FIG. 7, graph G71 is displayed in a line chart form in which the vertical axis corresponds to the unit "U/I", and the horizontal axis corresponds to the time axis. The time axis shown in FIG. 7 indicates a period of time from "20170423 00:00" to "20170517 24:00".

According to FIG. 7, the processing circuitry 11 causes the display 13 to display the medical examination data items classified under "AST(GOT)-second display" of the medical examination data items shown in FIG. 5 as graph G72 on one line in an upper region different from the region including graph G71. The processing circuitry 11 causes the display 13 to display elements corresponding to the medical examination data items included in graph 72 by using the time axis included in the region including graph 71.

According to FIG. 7, the processing circuitry 11 causes the display 13 to display not only the time information indicated by the time axis, but also information on the unit "U/I" of the vertical axis, for the medical examination data items classified under the same classification group "AST (GOT)-first display" as the reference data item. In contrast, the processing circuitry 11 causes the display 13 to display only time information indicated by the time axis for the medical examination data items with the same item name (item ID) as the reference data item, but with a different unit from the reference data item, i.e., the medical examination data items classified into classification group "AST(GOT)-second display". In this way, regarding medical examination data items classified under a display style different from that of the reference data item, medical examination data items obtained in a wider variety of conditions can be simultaneously displayed by disregarding the information of the vertical axis.

Accordingly, the user can recognize that the medical examination data items represented by graph G71 are obtained in a different environment from the medical examination data items represented by graph G72.

The user can ascertain detailed information of each element included in graph G72 as text by pointing a cursor CR7 shown in FIG. 7 to the element (placing the cursor CR7 on the element) via, for example, the input interface 12. In FIG. 7, the cursor CR7 is pointed to the medical examination data item with item ID "0010" and measurement time "20170501 10:15" shown in FIG. 5, which is classified under "AST (GOT)-second display", and detailed information on that medical examination data item is displayed in the form of balloon B7. "2017-May-01 10:15 AST(GOT):3.6IU/I" is shown in balloon B7 shown in FIG. 7. Accordingly, the user can recognize that the unit of the medical examination data items represented by graph G71 is different from that of the medical examination data items represented by graph G72.

The processing circuitry 11 does not cause the display 13 to display the medical examination data items with an item name (item ID) different from the designated item name (item ID), i.e., the medical examination data items classified under "CREA-first display" in step SA8 shown in FIG. 4, among the medical examination data items shown in FIG. 5.

The processing circuitry 11 can also cause the display 13 to display medical examination data items for which a display method has been determined by the medical server 2 in another display form.

Figure 8:
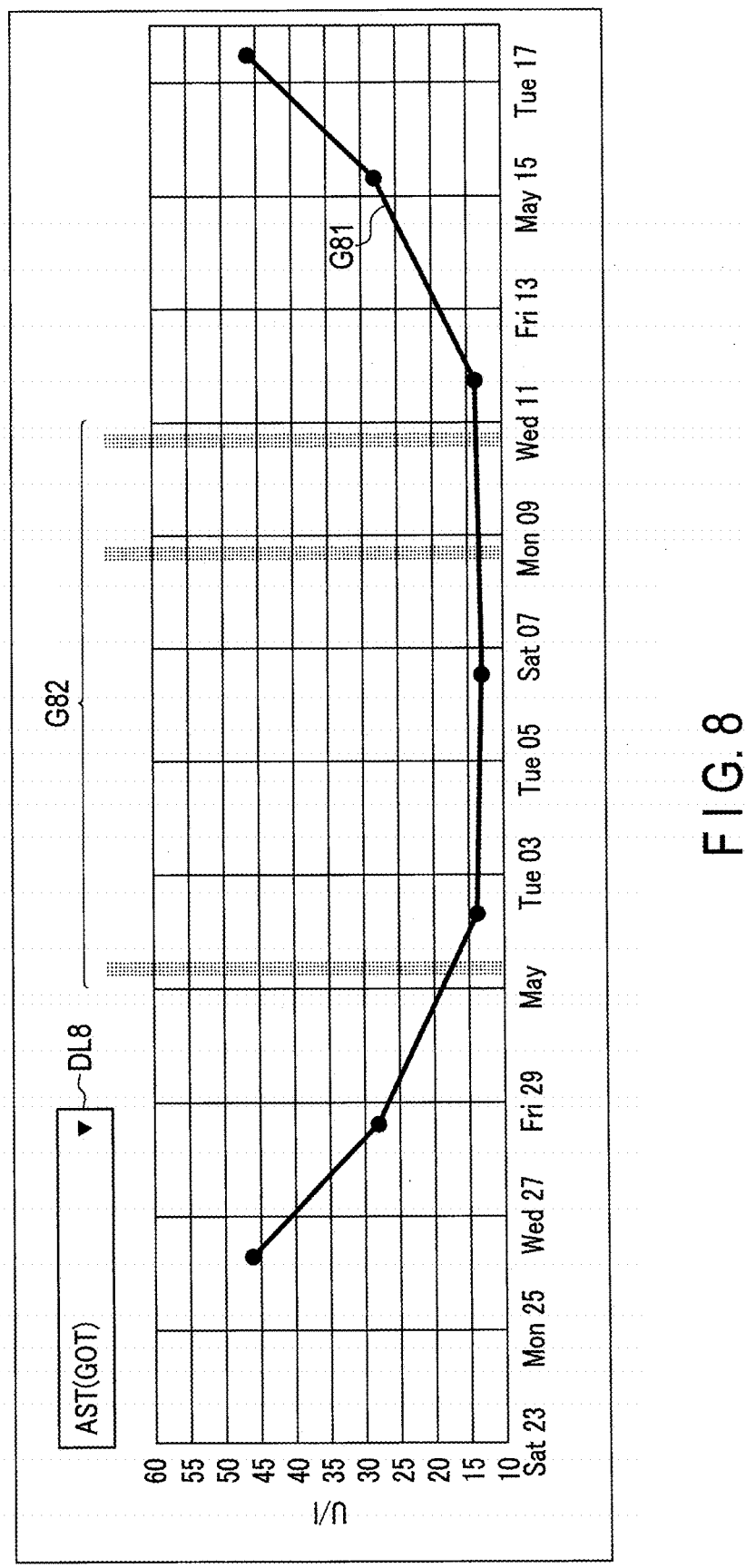
FIG. 8 is a diagram showing an example of the display screen displayed on the display of the medical terminal shown in FIG. 2.

FIG. 8 is a diagram showing an example of medical examination data items displayed on the display of the medical terminal shown in FIG. 2. The medical examination data items shown in FIG. 8 represent results of laboratory tests for, for example, patient ID "P0001". In the case of FIG. 8, for example, when one of the item names included in the drop-down list DL8 is designated, the processing circuitry 11 causes the display 13 to display test results corresponding to the designated item name. In the case of FIG. 8, "AST(GOT)" is designated.

According to FIG. 8, the processing circuitry 11 causes the display 13 to display the medical examination data items classified under "AST(GOT)-first display" as graph G81. In FIG. 8, graph G81 is displayed in a line chart form in which the vertical axis corresponds to the unit "U/I", and the horizontal axis corresponds to the time axis. The time axis shown in FIG. 8 indicates a period of time from "20170423 00:00" to "20170517 24:00".

According to FIG. 8, the processing circuitry 11 causes the display 13 to display the medical examination data items classified under "AST(GOT)-second display" of the medical examination data items shown in FIG. 5 on the time axis for graph G81. The processing circuitry 11 causes the display 13 to display the medical examination data items classified under "AST(GOT)-second display" as graph G82 in a bar chart form, which is different from the line chart form of graph G81, in the region including graph G81.

The processing circuitry 11 may convert the unit "IU/I" of the medical examination data items classified under "AST (GOT)-second display" into "U/I" and cause the display 13 to display the medical examination data items classified under "AST(GOT)-second display" together with the medical examination data items classified under "AST(GOT)-first display".

Figure 9:
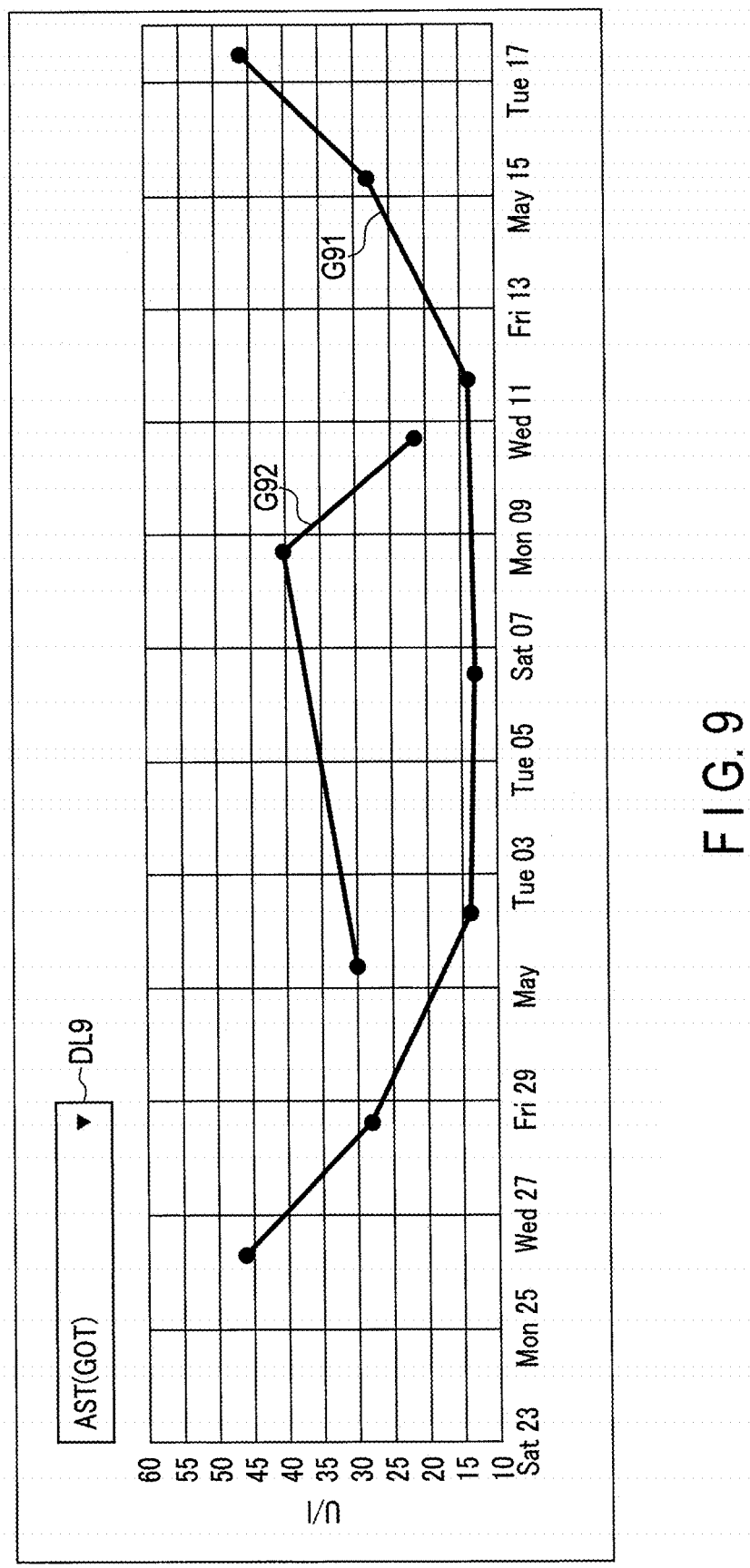
FIG. 9 is a diagram showing an example of the display screen displayed on the display of the medical terminal shown in FIG. 2.

FIG. 9 is a diagram showing an example of medical examination data items displayed on the display of the medical terminal shown in FIG. 2. The medical examination data items shown in FIG. 9 represent results of laboratory tests for, for example, patient ID "P0001". In the case of FIG. 9, for example, when one of the item names included in the drop-down list DL9 is designated, the processing circuitry 11 causes the display 13 to display test results corresponding to the designated item name. In the case of FIG. 9, "AST(GOT)" is designated.

According to FIG. 9, the processing circuitry 11 causes the display 13 to display the medical examination data items classified under "AST(GOT)-first display" as graph G91. In FIG. 9, graph G91 is displayed in a line chart form in which the vertical axis corresponds to the unit "U/I", and the horizontal axis corresponds to the time axis. The time axis shown in FIG. 9 indicates a period of time from "20170423 00:00" to "20170517 24:00".

According to FIG. 9, the processing circuitry 11 causes the display 13 to display the medical examination data items classified under "AST(GOT)-second display" of the medical examination data items shown in FIG. 5 as graph G92 on the time axis for graph G91. At this time, the processing circuitry 11 causes the display 13 to display graph G92 in the region including graph G91 in a form distinguishable from the form of graph G91.

According to FIG. 9, the processing circuitry 11 causes the display 13 to display not only the time information indicated by the time axis, but also information on the unit "U/I" of the vertical axis, for the medical examination data items classified under both "AST(GOT)-first display" and "AST(GOT)-second display". This enables the user to visually recognize the medical examination data items classified under "AST(GOT)-second display" while directly comparing them with the medical examination data items classified under "AST(GOT)-first display".

According to the first embodiment, the processing circuitry 23 included in the medical server 2 extracts data attributes relating to medical examination data items stored in relation to a patient. The processing circuitry 23 calculates a similarity between a designated medical examination data item and another medical examination data item of a plurality of stored medical examination data items based on the data attributes of the medical examination data items. The processing circuitry 23 classifies each medical examination data item into one of a plurality of classification groups based on the calculated similarity. The processing circuitry 23 generates a display screen of a graph in which classified medical examination data items are plotted in display forms distinguishable between classification groups on a common time axis.

Accordingly, the user who refers to medical examination data items displayed in accordance with a determined display method can also refer to medical examination data items having some different data attributes due to the difference in the environment of obtainment, but in short distances representing similarities with the reference data item. Therefore, the user can ascertain more information meaningful in medical examination. The user can also recognize that the data attributes of medical examination data items are different, for example, from the difference in the determined display method. This decreases the possibility of false recognition of displayed medical examination data items by the user.

In addition, in the case where there is a mixture of medical examination data items obtained in different environments, for example, with different apparatuses or difference settings, if the stored medical examination data items are automatically integrated and displayed, they may be wrongly integrated, which causes a safety risk. Such a problem is prominent when medical examination data items stored in a plurality of facilities are integrated and displayed. With the medical server 2 according to the first embodiment, medical examination data items classified into classification groups related to each other are comprehensively displayed in classification group units, the safety risk caused by oversight of data or wrong data integration can be reduced.

(First Modification)

In the first embodiment, the processing circuitry 23 included in the medical server 2 classifies medical examination data items having numerical values as measurements;

however, the configuration is not limited to this. The processing circuitry 23 may classify medical examination data items having non-numerical values, such as character strings, under display styles.

FIG. 10 is a diagram showing medical examination data items each accompanied by a series of data attributes in the first modification. FIG. 10 shows ten medical examination data items. According to FIG. 10, each medical examination data item has data attributions such as a measurement and a measurement time accompanying the measurement. The medical examination data set shown in FIG. 10 includes, for example: a medical examination data item constituted by measurement time "20170426 09:15" and measurement "−"; a medical examination data item constituted by measurement time "20170428 15:30" and measurement "+"; a medical examination data item constituted by measurement time "20170501 10:15" and measurement "3.6"; a medical examination data item constituted by measurement time "20170502 09:00" and measurement "++"; a medical examination data item constituted by measurement time "20170506 14:45" and measurement "++"; a medical examination data item constituted by measurement time "20170508 21:30" and measurement "3.8"; a medical examination data item constituted by measurement time "20170510 21:30" and measurement "4.5"; a medical examination data item constituted by measurement time "20170511 21:30" and measurement "+"; a medical examination data item constituted by measurement time "20170515 09:00" and measurement "−"; and a medical examination data item constituted by measurement time "20170517 14:45" and measurement "−".

At this time, the processing circuitry 23 included in the medical server 2 shown in FIG. 3 classifies the medical examination data items shown in FIG. 10 in accordance with the types of measurements. The processing circuitry 23 classifies the medical examination data items by using, for example, a correspondence table indicating the relationship between measurements and display styles. For example, the processing circuitry 23 classifies a medical examination data item having a numerical value as the measurement under the first display style, a medical examination data item having "++" as the measurement under the second display style, a medical examination data item having "+" as the measurement under the third display style, and a medical examination data item having "−" as the measurement under the fourth display style. The processing circuitry 23 generates display screen data based on the classification results. The display screen data represents a display screen of a graph in which classified medical examination data items are plotted in display forms distinguishable between classification groups on a common time axis.

The processing circuitry 23 transmits the generated display screen data to the medical terminal 1 via, for example, the communication interface 21.

Upon receipt of the display screen data transmitted from the medical server 2, the processing circuitry 11 of the medical terminal 1 shown in FIG. 2 executes the display control function 112. Through the display control function 112, the processing circuitry 11 causes the display 13 to display a display screen based on the display screen data.

FIG. 11 is a diagram showing an example of the display screen displayed on the display 13 of the medical terminal 1 shown in FIG. 2 in the first modification. In FIG. 11, the medical examination data items shown in FIG. 10 are classified under predetermined display styles and shown along a common time axis.

In FIG. 11, the medical examination data items classified under the first display style are plotted on one line segment of "numerical value" by double circles. The medical examination data items classified under the second display style are plotted on one line segment of "++" by filled circles. The medical examination data items classified under the third display style are plotted on one line segment of "+" by filled circles. The medical examination data items classified under the third display style are plotted on one line segment of "−" by filled circles.

According to the first modification, the processing circuitry 23 included in the medical server 2 classifies medical examination data items including non-numerical values as measurements under display styles. This enables the user to ascertain a wider variety of information meaningful in medical examination.

(Second Modification)

Described in the first embodiment is the case where the similarity is calculated and the display method is determined based on the item name (item ID) and unit of the data attributes; however, the configuration is not limited to this. In the second modification, the similarity is calculated and the display method is determined based on, for example, the "measurement" and data attributes "tester" and "apparatus name" of the measurement of imaging test (echo) as well as the item name (item ID) and unit.

FIG. 12 is a diagram for explaining an operation of the processing circuitry 23 of the medical server 2 shown in FIG. 3 in the second modification. In the case of FIG. 12, let us assume that the distance of when data attribute "item ID" is different, the distance of when data attribute "apparatus name" is different, the distance of when data attribute "tester" is different, and the distance of when the "measurement" is an outlier which is largely different from the measurement of the reference data item are set in advance as "10", "5", "2", and "1", respectively, by a predetermined method. In addition, in the flowchart shown in FIG. 4, let us assume that threshold A and threshold B are set in advance at 5 and 1, respectively. Namely, the processing circuitry 23 determines that a medical examination data item with different "tester" has high similarity and classifies it under, for example "second display style", but determines that a medical examination data item with a different "apparatus name" has low similarity and classifies it as a medical examination data item different from the reference data item. A medical examination data item with a "measurement" largely different from those of the other medical examination data items is classified under the "second display style" as being measured under a different condition or as involving a measurement error, even if the data attributes are the same.

In the following description, let us assume that the medical examination data items designated as display subjects are those of the same patient ID, and there is no difference in the patient ID between the medical examination data items. Let us also assume that data attribute "unit" of all the medical examination data items designated as display subjects is "mm".

According to FIG. 12, each medical examination data item accompanied by a series of data attributes according to the second modification has, for example, a measurement and data characteristics accompanying the measurement. The data characteristics shown in FIG. 12 include, for example, a patient ID, an item ID, an item name, a measurement time, an apparatus name, a tester, and a unit. As shown in FIG. 12, the set of medical examination data items each accompanied by a series of data attributes according to the second modification includes, for example: a medical examination data item constituted by patient ID "P0001", item ID "0001", item name "left ventricular internal dimension in diastole (LVIDd) (2D)", measurement time "20170511 21:30", apparatus name "echo of manuf. A", tester "technician Y", measurement "34", and unit "mm"; a medical examination data item constituted by patient ID "P0001", item ID "0001", item name "LVDd", measurement time "20170515 09:00", apparatus name "echo of manuf. A", tester "technician Y", measurement "27", and unit "mm"; a medical examination data item constituted by patient ID "P0001", item ID "0001", item name "LVDd", measurement time "20170517 14:45", apparatus name "echo of manuf. A", tester "technician X", measurement "20", and unit "mm"; a medical examination data item constituted by patient ID "P0001", item ID "0010", item name "LVIDd(M)", measurement time "20170420 00:00", apparatus name "echo of manuf. A", tester "technician Y", measurement "36", and unit "mm"; a medical examination data item constituted by patient ID "P0001", item ID "0010", item name "LVIDd(M)", measurement time "20170426 09:15", apparatus name "echo of manuf. A", tester "technician X", measurement "26", and unit "mm"; a medical examination data item constituted by patient ID "P0001", item ID "0010", item name "LVIDd(M)", measurement time "20170428 15:30", apparatus name "echo of manuf. B", tester "technician X", measurement "29", and unit "mm"; a medical examination data item constituted by patient ID "P0001", item ID "0010", item name "LVIDd (M)", measurement time "20170429 10:15", apparatus name "echo of manuf. B", tester "technician X", measurement "37", and unit "mm"; a medical examination data item constituted by patient ID "P0001", item ID "0010", item name "LVIDd(M)", measurement time "20170501 00:00", apparatus name "echo of manuf. A", tester "technician Y", measurement "42", and unit "mm"; a medical examination data item constituted by patient ID "P0001", item ID "0010", item name "LVIDd(M)", measurement time "20170503 21:30", apparatus name "echo of manuf. A", tester "technician Y", measurement "120", and unit "mm"; and a medical examination data item constituted by patient ID "P0001", item ID "0010", item name "LVIDd(M)", measurement time "20170508 09:00", apparatus name "echo of manuf. A", tester "technician Y", measurement "39", and unit "mm".

In, for example, step SA4 of the flowchart shown in FIG. 4, the processing circuitry 23 included in the medical server 2 shown in FIG. 3 sets, as the reference data item, one medical examination data item with the most recent measurement time "20170508 09:00" of the medical examination data items with, for example, item name "LVIDd(M)" (item ID "0010") of the medical examination data items shown in FIG. 12. The item name is determined by user designation via, for example, the input interface 12.

The processing circuitry 23 repeats steps SA5 to SA12 shown in FIG. 4 for the remaining nine medical examination data items to be compared with the set reference data item, which are shown in FIG. 12.

Accordingly, as shown in FIG. 12, the distance between the reference data item and each of the medical examination data item with item ID "0001" and measurement time "20170511 21:30", the medical examination data item with item ID "0001" and measurement time "20170515 09:00", and the medical examination data item with item ID "0001" and measurement time "20170517 14:45" is calculated to be "10", "10", and "12", respectively. Accordingly, the medical examination data item with item ID "0001" and measurement time "20170511 21:30", the medical examination data item with item ID "0001" and measurement time "20170515 09:00", and the medical examination data item with item ID "0001" and measurement time "20170517 14:45" are classified under "LVDd-second display", "LVDd-second display", and "LVDd-first display", respectively.

Furthermore, as shown in FIG. 12, the distance between the reference data item and each of the medical examination data item with item ID "0010" and measurement time "20170420 00:00", the medical examination data item with item ID "0010" and measurement time "20170426 09:15", the medical examination data item with item ID "0010" and measurement time "20170428 15:30", the medical examination data item with item ID "0010" and measurement time "20170429 10:15", the medical examination data item with item ID "0010" and measurement time "20170501 00:00", and the medical examination data item with item ID "0010" and measurement time "20170503 21:30" is calculated to be "0", "2", "5", "5", "0", and "1", respectively. Accordingly, the medical examination data item with item ID "0010" and measurement time "20170420 00:00", the medical examination data item with item ID "0010" and measurement time "20170426 09:15", the medical examination data item with item ID "0010" and measurement time "20170428 15:30", the medical examination data item with item ID "0010" and measurement time "20170429 10:15", the medical examination data item with item ID "0010" and measurement time "20170501 00:00", and the medical examination data item with item ID "0010" and measurement time "20170503 21:30" are classified under "LVIDd(M)-first display", "LVIDd(M)-second display", "Manuf. B LVIDd(M)-first display", "Manuf. B LVIDd(M)-first display", "LVIDd(M)-first display", and "LVIDd(M)-second display", respectively.

After performing classification processing of nine medical examination data items, the processing circuitry 23 determines, for example, in step SA12 shown in FIG. 4, whether or not there is any other record left.

Since there is no other medical examination data item to be compared with the reference data item (No in step SA12 shown in FIG. 4), the processing circuitry 23 transmits the processing results to the Medical terminal 1 via, for example, the communication interface 21 (step SA13 shown in FIG. 4). Specifically, the processing circuitry 23 transmits the display method classification results of the medical examination data items, which include the medical examination data item set as the reference data item, to the medical terminal 1 via, for example, the communication interface 21.

Upon receipt of the display method classification results of the medical examination data items transmitted from the medical server 2, the processing circuitry 11 included in the medical terminal 1 receives designation of an item name of display subjects via, for example, the input interface 12. Upon receipt of designation of an item name of display subjects, for example, designation of item name "LVIDd (M)", the processing circuitry 11 executes the display control function 112 to cause the display 13 to display medical examination data items in accordance with the classification results received from the medical server 2.

Figure 13:
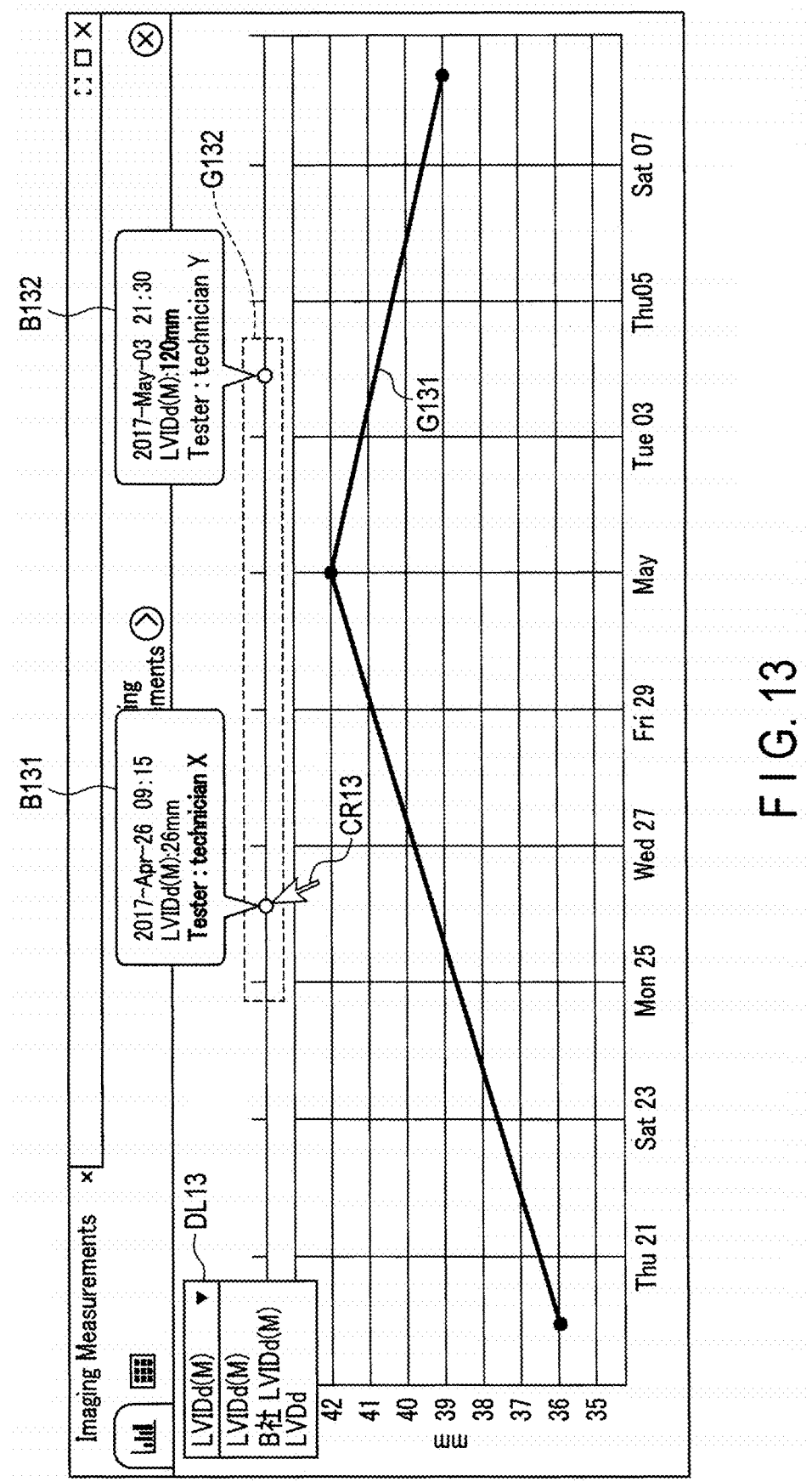
FIG. 13 is a diagram showing an example of the display screen displayed on the display of the medical terminal shown in FIG. 2 in the second modification.

FIG. 13 is a diagram showing an example of the display screen displayed on the display 13 of the medical terminal 1 shown in FIG. 2 in the second modification. The medical examination data items shown in FIG. 13 represent results of laboratory tests for, for example, patient ID "P0001". In the case of FIG. 13, when one of the item names included in, for example, the drop-down list DL13 is designated, the processing circuitry 11 causes the display 13 to display test results corresponding to the designated item name. With the drop-down list DL13 shown in FIG. 13, the display subject can be switched between, for example, "LVIDd(M)", "manuf B LVIDd(M)" and "LVDd". "LVIDd(M)" indicates that, for example, medical examination data items with item name "LVIDd(M)" and apparatus name "echo of manuf. A" are display subjects. "manuf. B LVIDd(M)" indicates that, for example, medical examination data items with item name "LVIDd(M)" and apparatus name "echo of manuf. B" are display subjects. "LVDd" indicates that, for example, medical examination data items with item name "LVDd" or "LVDd(2D)" and apparatus name "echo of manuf. A" are display subjects.

In the case of FIG. 13, "LVIDd(M)" is designated. Therefore, in the case of FIG. 13, the processing circuitry 11 causes the display 13 to show results of imaging tests corresponding to the designated "LVIDd(M)".

According to FIG. 13, the processing circuitry 11 causes the display 13 to display medical examination data items classified under "LVIDd(M)-first display" as graph G131. In FIG. 13, the graph G131 is displayed in a line chart form in which the vertical axis corresponds to the unit "mm", and the horizontal axis corresponds to the time axis. The time axis shown in FIG. 7 indicates a period of time from "20170419 00:00" to "20170508 24:00".

According to FIG. 13, the processing circuitry 11 also causes the display 13 to display medical examination data items classified under "LVIDd(M)-second display" of the medical examination data items shown in FIG. 12 as graph G132 on one line segment in an upper region which is different from the region including graph G131. The processing circuitry 11 displays elements corresponding to the medical examination data items included in graph G132 by using the time axis included in the region in which graph G131 is shown.

According to FIG. 13, the processing circuitry 11 causes the display 13 to display not only the time information indicated by the time axis, but also information on the unit "mm" of the vertical axis for the medical examination data items classified under the same classification group "LVIDd(M)-first display" as the reference data item. The processing circuitry 11 causes the display 13 to display only time information indicated by the time axis for the medical examination data items in which the item name (item ID) is the same as that of the reference data item but at least one of the "unit", "examination staff", or "measurement" is different from that of the reference data item, i.e., the medical examination data items classified into classification group "LVIDd(M)-second display". In this way, regarding medical examination data items classified under a different display style from the display style of the reference data item, medical examination data items obtained in a wider variety of conditions can be simultaneously displayed by omitting information of the vertical axis.

Accordingly, the user can recognize that the medical examination data items represented by graph G131 are obtained in a different environment from the medical examination data items represented by graph G132.

At this time, the user can ascertain detailed information of each element included in graph G132 by text by pointing a cursor CR13 shown in FIG. 7 to the element (placing the cursor CR7 on the element) via, for example, the input interface 12.

In FIG. 13, the cursor CR13 is pointed to the medical examination data item with item ID "0010" and measurement time "20170426 09:15" shown in FIG. 12, which is classified under "LVIDd(M)-second display". Detailed information on the medical examination data item is displayed in the form of balloon B131. Character string "2017-Apr-26 09:15 LVIDd(M):26mm" is shown in balloon B131 shown in FIG. 13. Character string "tester: technician X" is also shown in bold type in balloon B131 shown in FIG. 13. Accordingly, the user can recognize that the tester of the medical examination data items represented by graph G131 is different from that of the medical examination data item which cursor CR13 points to. Character string "tester: technician X" may be shown in a different color from the other character strings in balloon B131.

As shown in FIG. 13, detailed information on the medical examination data item with item ID "0010" and measurement time "20170503 21:30" shown in FIG. 12 is shown in the form of balloon B132 by being pointed to by cursor CR13. Character string "2017-May-03 21:30 LVIDd(M): 120mm" is shown in balloon B132 shown in FIG. 13. Of the character string "2017-May-03 21:30 LVIDd(M):120mm", "120mm" is shown in bold type. Accordingly, the user can recognize that, for example, the measurement of the medical examination data item which cursor CR13 points to largely differs from the measurements of the medical examination data items shown by graph G131, for example, the measurement is determined as an abnormal value. Character string "120mm" may be shown in a different color from the other character strings in balloon B132.

The processing circuitry 11 prevents the display 13 from displaying medical examination data items with a different item name (item ID) from the reference data item, i.e., medical examination data items classified under "LVDd-first display" and "LVDd-second display" as being different from the reference data item in step SA8 shown in FIG. 4, among the medical examination data items shown in FIG. 12.

The processing circuitry 11 also prevents the display 13 from displaying medical examination data items with apparatus name "echo of Manuf. B", which is different from apparatus name "echo of manuf. A" of the reference data item, i.e., medical examination data items classified under "manuf. B LVIDd(M)-first display", among the medical examination data items shown in FIG. 12.

(Third Modification)

Described in the first embodiment is the case where medical examination data items belonging to two different classification groups are displayed in different display styles. However, the number of displayed classification groups is not limited to two. In the third modification, the case where medical examination data items of three or more different classification groups are displayed in different display styles will be described. In this case, the processing circuitry 23 of the medical server 2 shown in FIG. 3 generates, for example, such display screen data that, for example, four different classification groups, which includes the classification group into which the reference data item is classified, are displayed in different display styles. In the following description, let us assume that the processing circuitry 23 classifies the medical examination data items with item name "AST(GOT)" under four classification groups: "AST(GOT)-first display", "AST(GOT)-second display", "AST(GOT)-third display", and "AST(GOT)-fourth display" by using, for example, four threshold values. Let us also assume that the medical examination data items classified under "AST(GOT)-first display" include the reference data item. Based on the classification results, the processing circuitry 23 generates display screen data representing a display screen of a graph in which medical examination data items classified under display forms distinguishable between classification groups are plotted on a common time axis. The processing circuitry 23 transmits the generated display screen data to the medical terminal 1.

Figure 14:
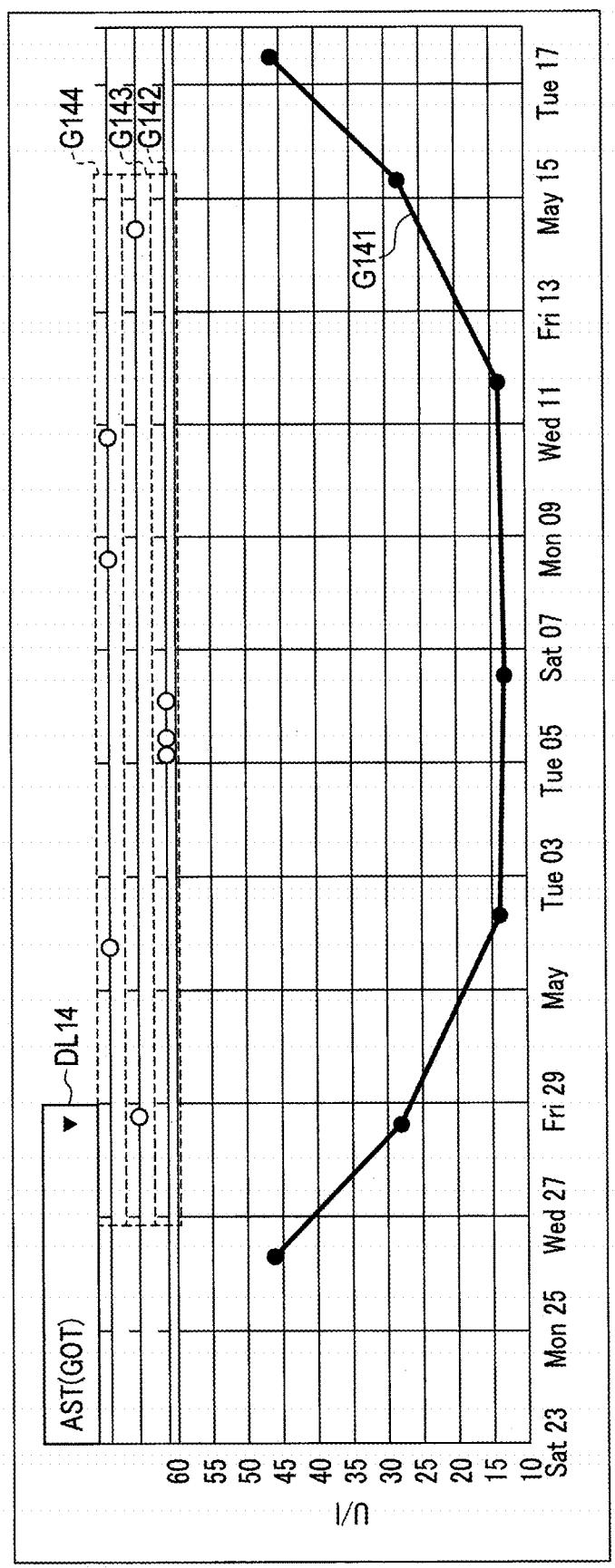
FIG. 14 is a diagram showing an example of the display screen displayed on the display of the medical terminal shown in FIG. 2 in the third modification.

FIG. 14 is a diagram showing an example of the display screen displayed on the display 13 of the medical terminal 1 shown in FIG. 2 in the third modification. The medical examination data items shown in FIG. 14 represent results of laboratory tests for, for example, patient ID "P0001". In the case of FIG. 14, when one of the item names included in, for example, the drop-down list DL14 is designated, the processing circuitry 11 causes the display 13 to display test results corresponding to the designated item name. In the case of FIG. 14, "AST(GOT)" is designated.

According to FIG. 14, the processing circuitry 11 causes the display 13 to display, for example, medical examination data items classified under "AST(GOT)-first display" as graph G141. The medical examination data items shown as graph G141 include the reference data item. In FIG. 14, graph G141 is displayed in a line chart form in which the vertical axis corresponds to the unit "U/I", and the horizontal axis corresponds to the time axis. The time axis shown in FIG. 14 indicates a period of time from "20170423 00:00" to "20170517 24:00".

The display screen based on the display screen data shown in FIG. 14 includes graphs G142, G143, and G144 as well as graph G141, which includes the reference data item. Graph G142 represents medical examination data items classified under, for example, "AST(GOT)"-second display". Graph G143 represents medical examination data items classified under, for example, "AST(GOT)"-third display". Graph G144 represents medical examination data items classified under, for example, "AST(GOT)"-fourth display".

According to the third modification, the processing circuitry 23 included in the medical server 2 classifies medical examination data items into three or more different classification groups. The processing circuitry 23 also generates display screen data of a graph in which medical examination data items classified into three or more classification groups are plotted by display styles distinguishable between classification groups by using a common time axis. This enables the user in visual contact with the display screen based on the display screen data to ascertain more and more detailed information necessary for diagnosis.

(Fourth Modification)

Described with reference to, for example, FIGS. 4 to 14 of the first embodiment is the case where the processing circuitry 23 included in the medical server 2 generates, based on medical examination data items including measurements, display screen data representing a display screen of a graph in which the medical examination data items are plotted. However, the generated display screen data is not limited to that representing a display screen of a graph of medical examination data items including measurements. The fourth modification is the case where the processing circuitry 23 generates, based on medical examination data items including medical image data, display screen data representing a display screen of a graph of the medical examination data items.

Figure 15:
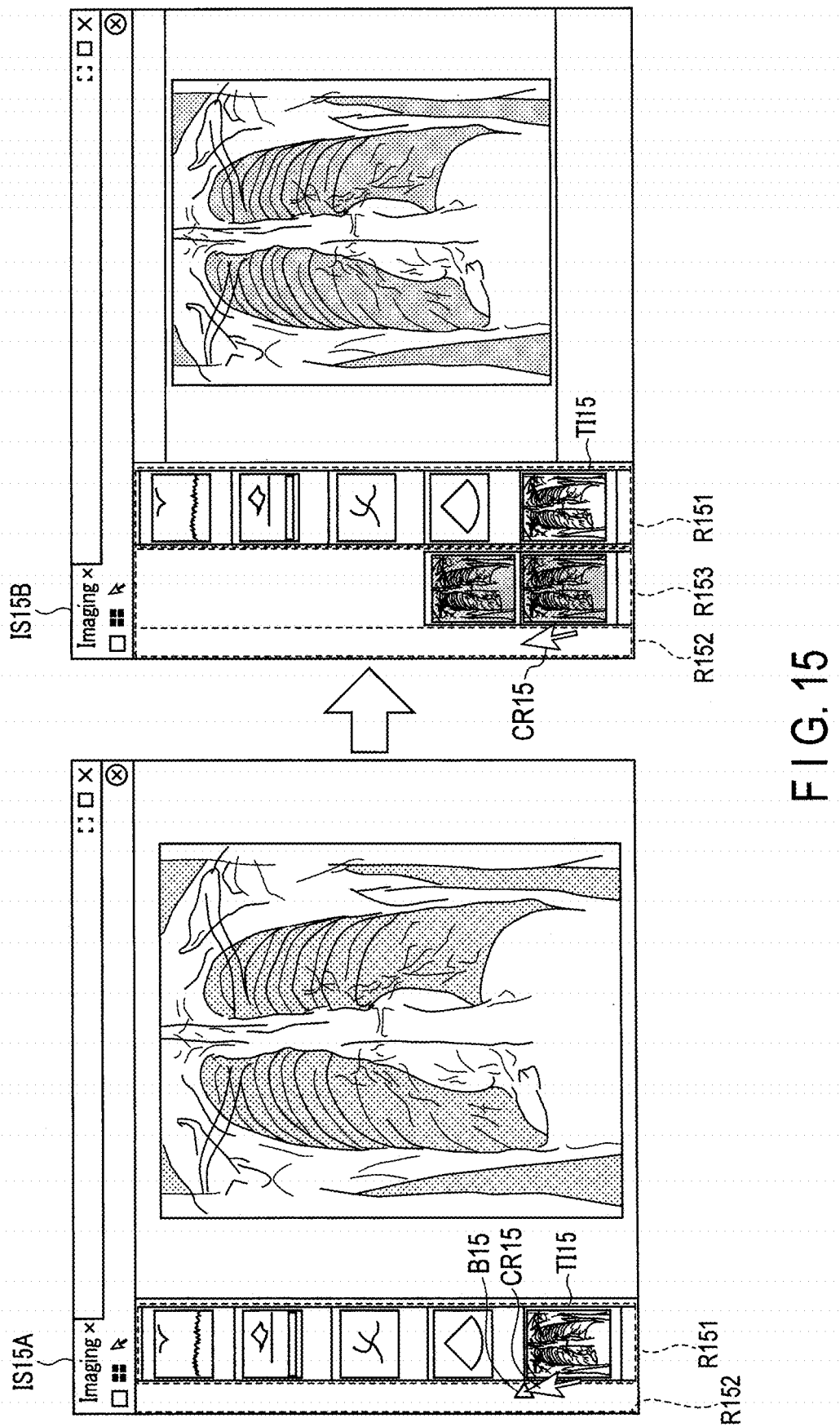
FIG. 15 is a diagram for explaining the display screen displayed on the display of the medical terminal shown in FIG. 2 in the fourth modification.

FIG. 15 is a diagram for explaining the display screen displayed on the display 13 of the medical terminal 1 shown in FIG. 2 in the fourth modification.

The display screen IS15A shown in FIG. 15 includes region 151 and region 152. Region 151 is a region in which a thumbnail image obtained by reducing the size of a medical image is displayed. Region 151 is a region in which a thumbnail image based on thumbnail image data item classified into, for example, a first classification group is displayed in a first display style. Region 151 includes, for example, a plurality of thumbnail images. The thumbnail images are aligned, for example, in time series in the vertical direction of the display screen. The thumbnail image data representing each thumbnail image includes time information.

Region 152 includes a button B15. Button B15 is a button for displaying, regarding thumbnail image TI15 serving as the reference image, a thumbnail image based on a thumbnail image data item classified into another classification group. For example, when button B15 is designated by cursor CR15, region R153 is newly displayed as shown in the display screen IS15B shown in FIG. 15. Region 153 is a region in which, in connection with, for example, thumbnail image Ti15, a thumbnail image based on a thumbnail image data item classified into a second classification group is displayed in a second display style. Region 153 includes, for example, a plurality of thumbnail images. The thumbnail images are aligned, for example, in time series in the vertical direction of the display screen. The thumbnail image data representing each thumbnail image includes time information.

In the fourth modification, the processing circuitry 23 generates, based on medical examination data items including medical image data, display screen data representing a display screen of a graph of the medical examination data items. This enables the user in visual contact with the display screen based on the display screen data to more visually ascertain the condition of the patient.

Second Embodiment

Described in the second embodiment is the case where the medical terminal 1 or the medical server 2 has not only the functions described in the first embodiment, but also a function of switching the display forms of displayed medical examination data items in units of classification groups. Described below is the case where the medical terminal 1 has the relevant function.

Figure 16:
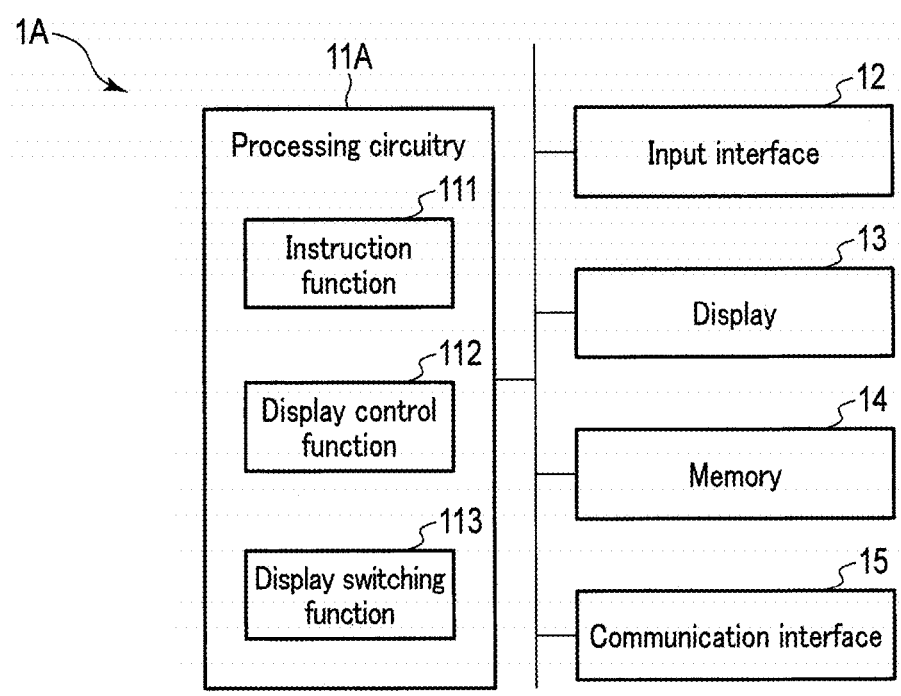
FIG. 16 is a block diagram showing a function configuration of a medical terminal according to the second embodiment.

FIG. 16 is a block diagram showing a function configuration of the medical terminal 1A according to the second embodiment. The medical terminal 1A shown in FIG. 16 includes processing circuitry 11A, an input interface 12, a display 13, a memory 14, and a communication interface 15. The processing circuitry 11A, the input interface 12, the display 13, the memory 14, and the communication interface 15 are connected in a communicative manner via, for example, a bus.

The processing circuitry 11A is a processor that functions as a nerve center of the medical terminal 1. The processing circuitry 11A executes a control program stored in, for example, the memory 14, thereby realizing a function corresponding to the program.

The configurations and functions of the input interface 12, display 13, memory 14, and communication interface 15 shown in FIG. 16 are the same as those of the input interface 12, display 13, memory 14, and communication interface 15 shown in FIG. 2.

The processing circuitry 11A according to the second embodiment has an instruction function 111, a display control function 112, and a display switching function 113.

The instruction function 111 and display control function 112 shown in FIG. 16 are the same as the instruction function 111 and display control function 112 shown in FIG. 2.

The display switching function 113 is a function of switching the display forms of displayed medical examination data items in units of classification groups. By executing the display switching function 113, the processing circuitry 11, for example, switches, integrates, or separates medical examination data items displayed on the display 13 in units of classification groups.

The instruction function 111, display control function 112, and display switching function 113 may be incorporated in the processing circuitry 11 as control programs or as dedicated hardware circuits capable of performing respective functions.

Figure 17:
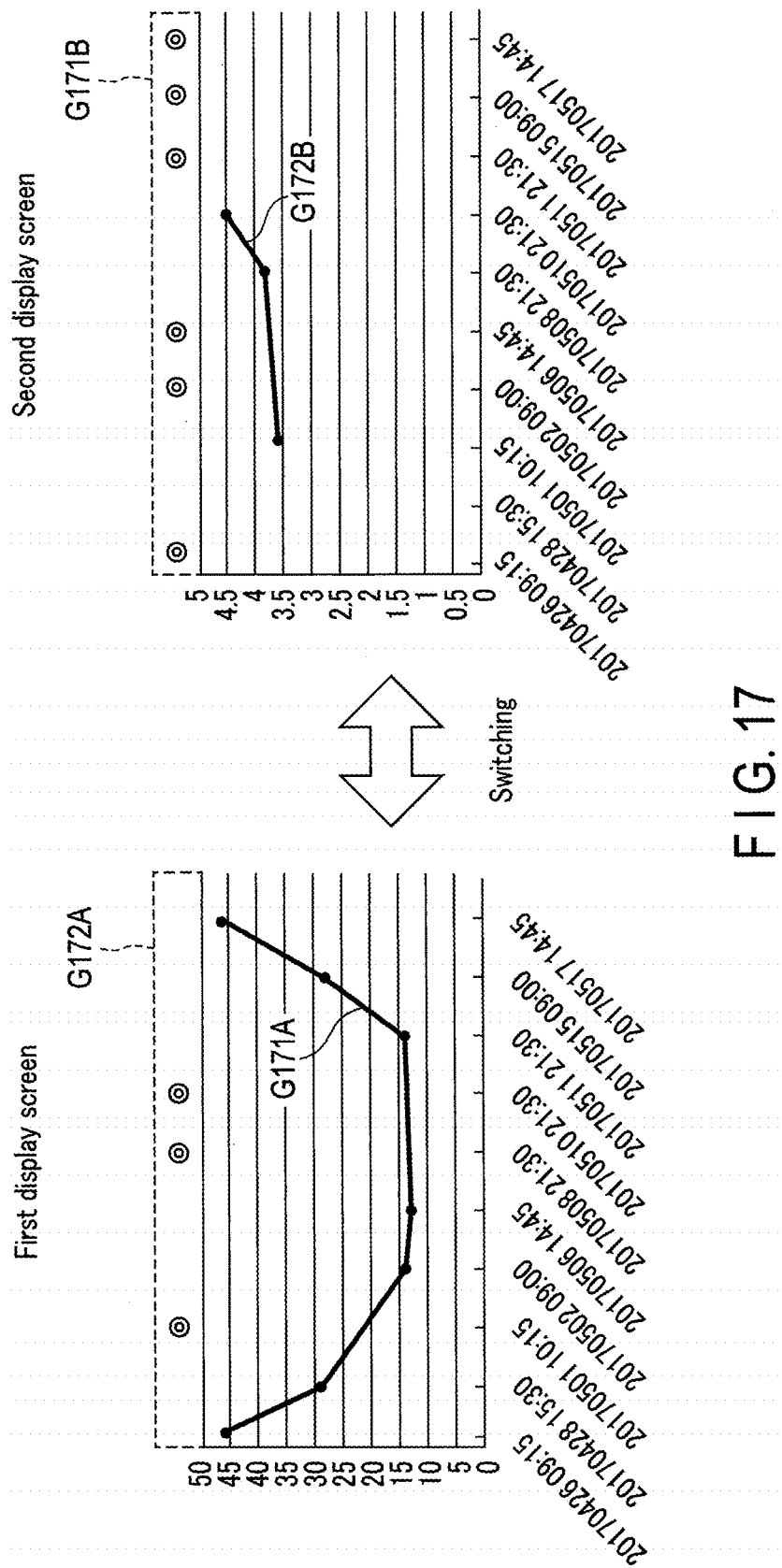
FIG. 17 is a diagram for explaining switching of display forms in the display screen displayed on the display of the medical terminal shown in FIG. 16.

Next, details of the display switching function 113 will be described. The display switching function 113 is executed in response to an input of a predetermined display switching instruction via, for example, the input interface 12. At this time, the processing circuitry 11A, for example, switches the displayed medical examination data items between classification groups. FIG. 17 is a diagram for explaining switching of the display forms in the display screen displayed on the display 13 of the medical terminal 1A shown in FIG. 16.

According to FIG. 17, the processing circuitry 11A can switch the display screen between the first display screen and the second display screen. The first display screen shown in FIG. 17 includes line graph G171A and point graph G172A. The second display screen shown in FIG. 17 includes line graph G172B and point graph G171B. Line graph G171A included in the first display screen and line graph G172B included in the second display screen use, for example, a common displayed time axis (period of time), but different display scales of measurements.

For example, when the first display screen is displayed, upon input of a predetermined display switching instruction, the processing circuitry 11A performs display switching processing so that the medical examination data items displayed by line graph G171A in the first display screen are displayed in the display form of point graph 171B in the second display screen. The processing circuitry 11A also performs display switching processing so that the medical examination data items displayed by line graph G172B in the first display screen are displayed in the display form of point graph 171B in the second display screen. The display switching processing is realized by, for example, the processing circuitry 11A generating display screen data of new display forms in accordance with a predetermined display switching instruction. The display switching processing may be realized by the processing circuitry 11A providing the medical server 2, via the communication interface 15, with an instruction to generate display screen data of new display forms.

The display switching as in FIG. 17 enables the user to ascertain, for example, details of the medical examination data items in a desired classification group of the medical examination data items of a plurality of classification groups. It is also advantageous in terms of easier viewing because details of only the medical examination data items belonging to some classification groups are displayed.

The processing circuitry 11A may, for example, integrate or separate the displayed medical examination data items in units of classification groups upon receipt of a predetermined display switching instruction. FIG. 18 is a diagram for explaining other switching of display forms in the display screen displayed on the display 13 of the medical terminal 1A shown in FIG. 16.

According to FIG. 18, the processing circuitry 11A can switch the display screen between a pre-integration display screen and a post-integration display screen. The pre-integration display screen shown in FIG. 18 includes line graph G181 and point graph G182. Line graph G181 represents, for example, medical examination data items belonging to the classification group into which the reference data item is classified. Point graph G182 represents, for example, medical examination data items not belonging to the classification group into which the reference data item is classified, but having the same item name as the reference data item.

The post-integration display screen shown in FIG. 18 includes line graph G183. Line graph G183 is a line graph obtained by integrating point graph G182 into line graph G181. Upon integration, the display scale of the measurements of the medical examination data items included in point graph G182 is conformed to the display scale of the measurements of the medical examination data items included in line graph G181. Line graph G181 included in the pre-integration display screen and line graph G183 included in the post-integration display screen use, for example, a common displayed time axis (period of time) and display scale of measurements.

The display switching as in FIG. 18 enables the user to ascertain, for example, medical examination data items in a plurality of classification groups by one graph, as needed.

How to integrate the graphs is not limited to displaying two graphs displayed in different graph regions in a common region as one graph. For example, two graphs shown in different regions may be displayed as different graphs in a common region.

Figure 19:
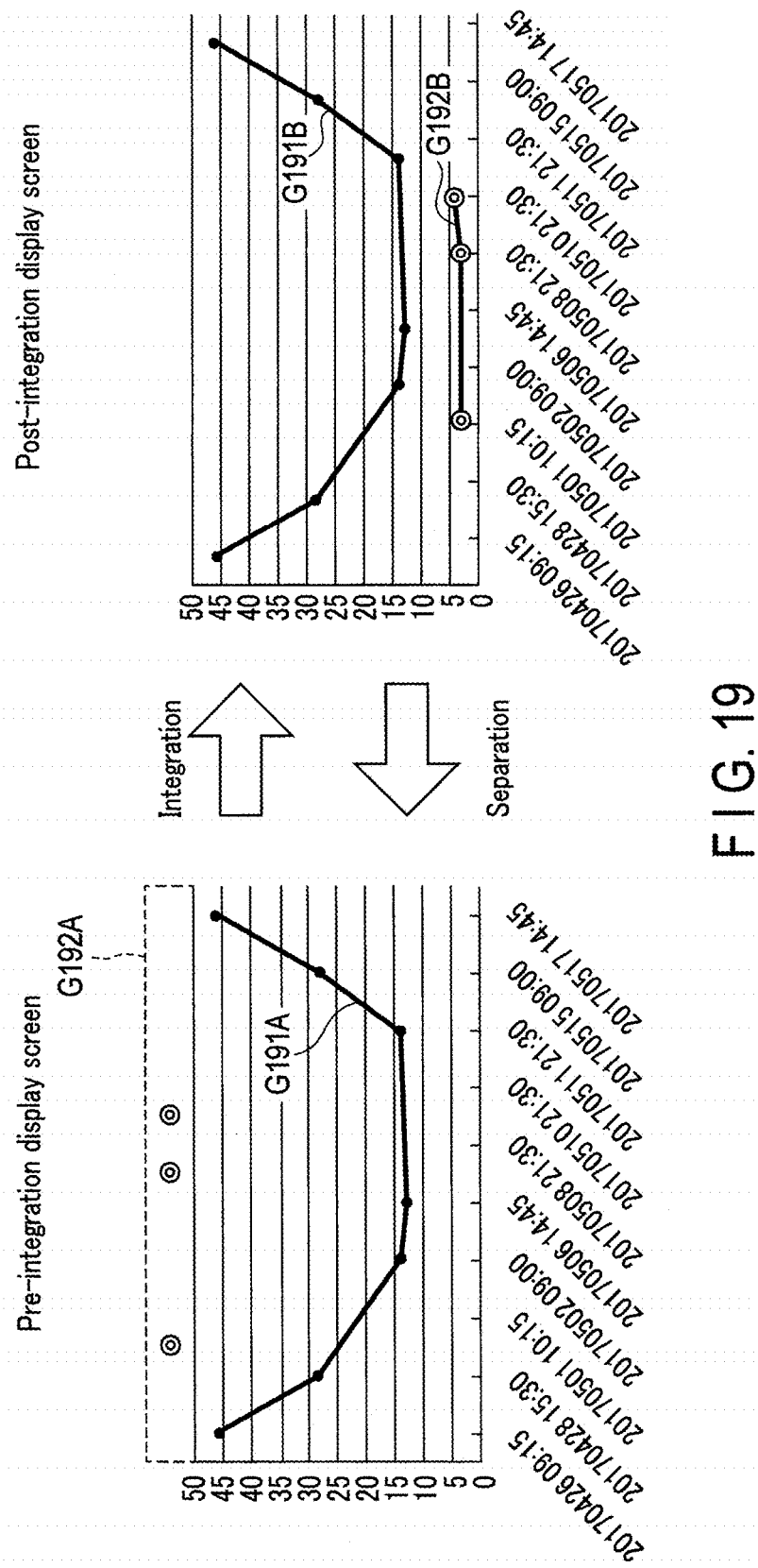
FIG. 19 is a diagram for explaining other switching of display forms in the display screen displayed on the display of the medical terminal shown in FIG. 16.

FIG. 19 is a diagram for explaining other switching of display forms in the display screen displayed on the display 13 of the medical terminal 1A shown in FIG. 16. According to FIG. 19, the processing circuitry 11A can switch the display screen between the pre-integration display screen and the post-integration display screen. The pre-integration display screen shown in FIG. 19 includes line graph G191A and point graph G192A. Line graph G191A represents, for example, medical examination data items belonging to the classification group into which the reference data item is classified. Point graph G192A represents, for example, medical examination data items not belonging to the classification group into which the reference data item is classified, but having the same item name as the reference data item.

The post-integration display screen shown in FIG. 19 includes line graph G191B and line graph G192B. Line graph G191B and line graph G192B are displayed as different graphs in one region in which the graphs share a common displayed time axis (period of time) and display scale of measurements. Line graph G191B is the same as line graph G191A. Upon integration, the display scale of the measurements of the medical examination data items included in point graph G192A is conformed to the display scale of the measurements of the medical examination data items included in line graph G191A.

The switching operation may include, for example, an operation to remove medical examination data items from the display subjects or to add medical examination data items as new display subjects in units of classification groups.

FIG. 20 is a diagram for explaining other switching of display forms in the display screen displayed on the display 13 of the medical terminal 1A shown in FIG. 16. According to FIG. 20, the processing circuitry 11A can switch the display screen between the first display screen and the second display screen. The first display screen shown in FIG. 20 includes line graph G201A and point graph G202A. The second display screen shown in FIG. 20 includes only line graph G201B. Line graph G201B is the same as line graph G201A. Namely, as shown in FIG. 20, upon switching from the first display screen to the second display screen, point graph G202A is deleted. Furthermore, as shown in FIG. 20, upon switching from the second display screen to the first display screen, point graph G202A is added.

Another Embodiment

In the above-embodiments, the medical terminal 1 and medical server 2 shown in FIG. 1 constitute, for example, a client server system in which the medical terminal 1 functions as a client, and the medical server 2 functions as a server; however, the configuration is not limited this. For example, various processing for generating display screen data may be performed on the medical terminal side.

Figure 21:
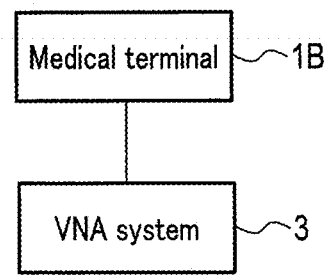
FIG. 21 is a block diagram showing a medical information system including a medical terminal according to another embodiment.

FIG. 21 is a block diagram showing an example of the environment in which a medical terminal 1B according to another embodiment is used. The medical terminal 1B shown in FIG. 21 is, for example, an apparatus capable of integratively observing medical information. For example, an integrative viewer is installed in the medical terminal 1B. The integrative viewer is an application for integratively presenting medical information to the user. The integrative viewer may be embodied as, for example, a web application, a fat client application, or a thin client application. The medical terminal 1B is an example of the medical information processing apparatus recited in the claims.

The medical terminal 1B is connected to, for example, a VNA system 3 shown in FIG. 21 via an intra-hospital network, such as a local area network (LAN), in a communicative manner.

The configuration and function of the VNA system 3 shown in FIG. 21 are the same as those of the VNA system 3 shown in FIG. 1.

Figure 22:
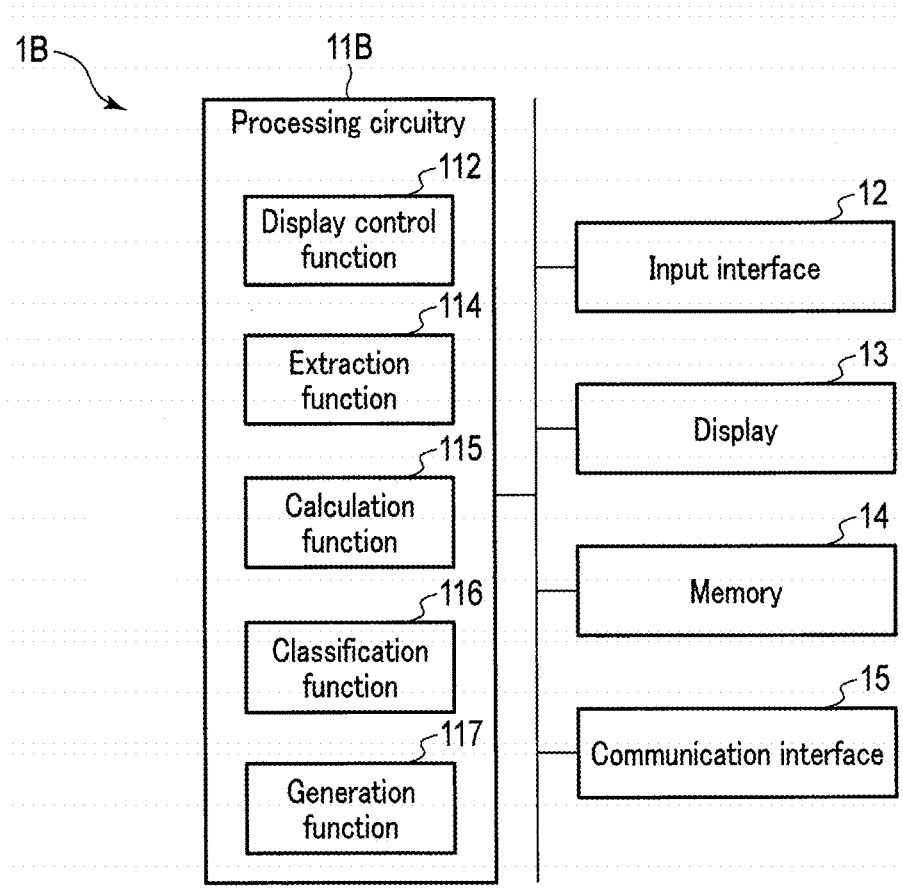
FIG. 22 is a block diagram showing a functional configuration of the medical terminal shown in FIG. 21.

Next, details of the medical terminal 13 according to another embodiment will be described with reference to FIG. 22. FIG. 22 is a block diagram showing a functional configuration of the medical terminal 1B shown in FIG. 21.

The medical terminal 1B shown in FIG. 22 includes processing circuitry 11B, an input interface 12, a display 13, a memory 14, and a communication interface 15. The processing circuitry 11B, the input interface 12, the display 13, the memory 14, and the communication interface 15 are connected in a communicative manner via, for example, a bus.

The processing circuitry 11B is a processor that functions as a nerve center of the medical terminal 1B. The processing circuitry 11B executes a control program stored in, for example, the memory 14, thereby realizing a function corresponding to the program.

The configurations and functions of the input interface 12, display 13, memory 14, and communication interface 15 shown in FIG. 22 are the same as those of the input interface 12, display 13, memory 14, and communication interface 15 shown in FIG. 2.

The processing circuitry 11B according to another embodiment has a display control function 112, an extraction function 114, a calculation function 115, a classification function 116, and a generation function 117.

The role of the display control function 112 shown in FIG. 22 is the same as that of the display control function 112 shown in FIG. 2. The roles of the extraction function 114, calculation function 115, classification function 116, and generation function 117 shown in FIG. 22 are the same as those of the extraction function 231, calculation function 232, classification function 233, and generation function 234 shown in FIG. 3.

The operation of the processing circuitry 11B included in the medical terminal 1B which is configured as described above will be described in accordance with the procedure shown in FIG. 23.

The following description will be provided on the assumption that a display instruction to display a display screen concerning medical examinations on a specific patient is input via the input interface 12 of the medical terminal 1B.

Figure 23:
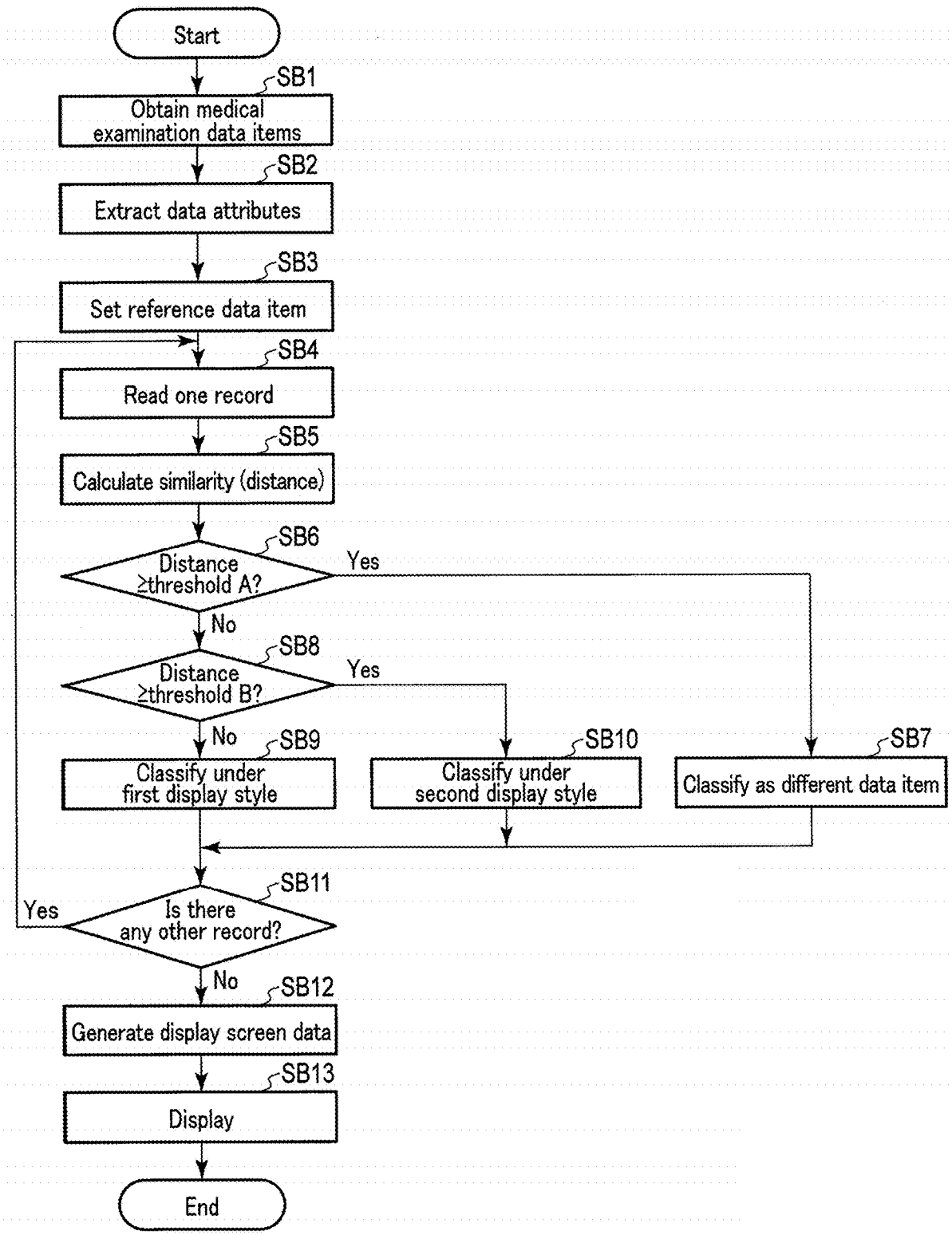
FIG. 23 is a flowchart showing a flow of processing performed by the processing circuitry included in the medical terminal shown in FIG. 20.

FIG. 23 is a flowchart showing a flow of processing performed by the processing circuitry 11B included in the medical terminal 1B shown in FIG. 22.

In the case of FIG. 23, upon receipt of the display instruction to display a display screen concerning medical examinations, the processing circuitry 11B, for example, obtains medical examination data items from the VNA system 3 by using information indicating a specific patient, which is included in the display instruction, as a key (step SB1).

The processing from step SB2 to step SB12 shown in FIG. 23 is the same as that from step SA3 to step SA13 shown in FIG. 4.

The processing circuitry 11B generates display screen data for each item name in step SB12 shown in FIG. 23, and then receives designation of an item name of display subjects via, for example, the input interface 12. Upon receipt of designation of an item name of display subjects, for example, designation of item "AST(GOT)", the processing circuitry 11B executes the display control function 112 and causes the display 13 to display a display screen based on the display screen data corresponding to item name "AST(GOT)".

In the above-described embodiments, medical examination data items not displayed by graph G71, but displayed in graph G72 in the second display style in a different region in the same display screen as shown in FIG. 7 are not limited to the ones described in the above embodiments. Medical examination data items included in the graph displayed in the second display style include medical examination data items identical in the item ID to the reference data item, but different only in the character string of the item name from the reference data item. An exemplary case is that the item name of the reference data item is "white count", whereas the item name of a medical examination data item different from the reference data item is "white blood cell (WBC)". The items names of the medical examination data items are different, but have the same item ID, and may indicate the same test item. Therefore, those medical examination data items may be observed at the same time.

Medical examination data items included in the graph displayed in the second display style also include medical examination data items with a different item ID from the reference data item, but a similar character string of the item name to the reference data item. An exemplary case is that the item name of the reference data item is "pH (urine)", whereas the item name of a medical examination data item different from the reference data item is "pH (arterial blood)" or "pH (venous blood)". The item names may indicate related test items, and medical examination data items with those item names may be referred to at the same time.

Medical examination data items included in the graph displayed in the second display style also include medical examination data items with greatly different acquisition dates. Those medical examination data items may be related to different test accuracies or test value references, and combining those medical examination data items into the same graph may cause a problem.

Medical examination data items included in the graph displayed in the second display style also include medical examination data items of different facilities in which a test is performed. If tests are performed in different facilities, the test values may be those obtained with reference to different test references.

Medical examination data items included in the graph displayed in the second display style also include medical examination data items of examinations by different examination staff. The examination values, etc. may largely differ when subjective evaluation is made by different evaluators.

Medical examination data items included in the graph displayed in the second display style also include medical examination data items of different apparatuses. The accuracies of the apparatuses may differ.

Medical examination data items included in the graph displayed in the second display style also include medical examination data items of different methods for obtaining measurements. An exemplary case is that the reference data item is obtained by "manual input", whereas a medical examination data item different from the reference data item is obtained by "automatic input". The medical examination data items may be influenced by test accuracy or an input error.

According to at least one of the above-described embodiments, efficiency in ascertaining medical examination data items obtained in various environments can be improved.

The term "processor" used in the above description means, for example, a central processing unit (CPU), a graphics processing unit (GPU), or circuitry such as an application specific integrated circuit (ASIC), a programmable logic device (e.g., a simple programmable logic device (SPLD), a complex programmable logic device (CPLD), or a field programmable gate array (FPGA). The processor realizes a function by reading and executing a program stored in memory circuitry. Each processor of the above-described embodiments is not necessarily configured as a single circuit, and a plurality of independent circuits may be configured in combination as one processor to realize the function. In addition, a plurality of structural elements in FIGS. 1 and 2 may be integrated in one processor to realize the function.

While some embodiments have been described, the embodiments have been presented as examples, and are not intended to limit the scope of the invention. Indeed, those novel embodiments described herein may be embodied in a variety of other forms; furthermore, various omissions, substitutions and changes may be made without departing from the spirit of the invention. The embodiments and their modifications are included in the scope and spirit of the invention and are included in the scope of the claimed inventions and their equivalents.

The invention claimed is:

1. A supporting apparatus comprising:
processing circuitry configured to:
extract attributes concerning a plurality of medical examination data items of a same type obtained from a same patient at different measurement times;
classify the medical examination data items into a first group that includes data items having high similarities to reference data and a second group that includes data items having low similarities to the reference data based on the attributes; and
generate a display screen that displays the classified medical examination data items on a common time axis in display forms distinguishable between the groups, and that displays values of the medical examination data items of the first group in a graph that shows changes over time along a time axis.

2. The supporting apparatus according to claim 1, wherein the processing circuitry
calculates similarities between a designated medical examination data item and other medical examination data items of the medical examination data items based on the attributes, and
classifies the medical examination data items in accordance with the similarities.

3. The supporting apparatus according to claim 2, wherein the processing circuitry classifies the medical examination data items into the first group, which includes the designated medical examination data item, and the second group, which includes at least one of the other medical examination data items.

4. The supporting apparatus according to claim 1, wherein the processing circuitry switches display forms of the displayed medical examination data items in units of the groups.

5. The supporting apparatus according to claim 1, wherein the medical examination data items concern a laboratory test or an imaging test.

6. The supporting apparatus according to claim 1, wherein the attributes include at least one of a patient ID, an item ID, an item name, a measurement time, an apparatus name, a tester, or a measurement unit.

7. A display system comprising:
processing circuitry configured to:
extract attributes concerning a plurality of medical examination data items of a same type obtained from a same patient at different measurement times;
classify the medical examination data items into a first group that includes data items having high similarities to reference data and a second group based on the attributes that includes data items having low similarities to the reference data;
generate a display screen that displays the classified medical examination data items on a common time axis in display forms distinguishable between the groups, and that displays values of the medical examination data items of the first group in a graph that shows changes over time along a time axis; and
cause a display to display the display screen.

8. The display system according to claim 7, wherein the processing circuitry
calculates similarities between a designated medical examination data item and other medical examination data items of the medical examination data items based on the attributes, and
classifies the medical examination data items in accordance with the similarities.

9. The display system according to claim 8, wherein the processing circuitry classifies the medical examination data items into the first group, which includes the designated medical examination data item, and the second group, which includes at least one of the other medical examination data items.

10. The display system according to claim 7, wherein the processing circuitry switches display forms of the displayed medical examination data items in units of the groups.

11. The display system according to claim 7, further comprising an input interface configured to receive designation of a test item,
wherein the processing circuitry causes the display to display only the medical examination data items with the designated test item.

12. A supporting method comprising:
extracting attributes concerning a plurality of medical examination data items of a same type obtained from a same patient at different measurement times;
classifying the medical examination data items into a first group that includes data items having high similarities to reference data and a second group that includes data items having low similarities to the reference data based on the attributes; and
generating a display screen that displays the classified medical examination data items on a common time axis in display forms distinguishable between the groups, and that displays values of the medical examination data items of the first group in a graph that shows changes over time along a time axis.

13. The supporting method according to claim 12, further comprising:
calculating similarities between a designated medical examination data item and other medical examination data items of the medical examination data items based on the attributes; and
classifying the medical examination data items based on the similarities.

14. The supporting method according to claim 12, wherein the medical examination data items are classified into the first group, which includes the designated medical examination data item, and the second group, which includes at least one of the other medical examination data items.

15. The supporting method according to claim 12, further comprising switching display forms of the displayed medical examination data items in units of the groups.

* * * * *